(12) United States Patent
Hackett et al.

(10) Patent No.: US 8,221,348 B2
(45) Date of Patent: Jul. 17, 2012

(54) EMBOLIC PROTECTION DEVICE AND METHODS OF USE

(75) Inventors: Steven S. Hackett, Maple Grove, MN (US); Eric S. Stainbrook, St. Paul, MN (US); Thomas F. Janecek, Flagstaff, AZ (US); Chad W. Trembath, Big Lake, MN (US); Andrew J. Dusbabek, Dayton, MN (US); John R. Drontle, Monticello, MN (US); Joel D. Phillips, Minneapolis, MN (US); Thomas V. Ressemann, St. Cloud, MN (US); Kyle L. Thunstrom, Eden Prairie, MN (US); Peter T. Keith, St. Paul, MN (US)

(73) Assignee: St. Jude Medical, Cardiology Division, Inc., Minneapolis, MN (US)

( * ) Notice: Subject to any disclaimer, the term of this patent is extended or adjusted under 35 U.S.C. 154(b) by 1866 days.

(21) Appl. No.: 11/177,473

(22) Filed: Jul. 7, 2005

(65) Prior Publication Data
US 2007/0010787 A1 Jan. 11, 2007

(51) Int. Cl.
*A61M 29/00* (2006.01)
(52) U.S. Cl. .............. 604/96.01; 604/131; 604/276; 604/173; 604/164.13
(58) Field of Classification Search .............. 604/131, 604/173, 276, 96.01, 164.13
See application file for complete search history.

(56) References Cited

U.S. PATENT DOCUMENTS
3,208,467 A 9/1965 Eichelman
(Continued)

FOREIGN PATENT DOCUMENTS
EP 0427429 5/1991
(Continued)

OTHER PUBLICATIONS

Hurst, Robert W., M.D., "Cartoid Angioplasty," Radiology, vol. 201, No. 3, Dec. 1996, pp. 613-616.
(Continued)

*Primary Examiner* — Nicholas Lucchesi
*Assistant Examiner* — Scott Medway
(74) *Attorney, Agent, or Firm* — Holland & Hart

(57) ABSTRACT

An evacuation sheath assembly and method of reducing or removing a blockage within a vessel without permitting embolization of particulate matter is provided. The evacuation sheath assembly includes a first elongate tubular member, having proximal and distal ends and a main lumen configured to be placed in fluid communication with a blood vessel. An expandable member is provided on a distal portion of the tubular member and is configured to form a seal with the blood vessel. The evacuation assembly further includes a second elongate tubular member having proximal and distal ends and an inflation lumen configured to be placed in fluid communication with the expandable member and a gas inflator. The gas inflator includes a high pressure gas source and a mechanism for regulating the pressure of the gas delivered by the gas inflator. The gas inflator is configured to be placed in fluid communication with the proximal end of the inflation lumen in order to provide a regulated pressure gas source for inflating the expandable member. A method of treatment of a blood vessel using the evacuation sheath assembly includes advancing the evacuation sheath assembly into the blood vessel through a guide catheter. The expandable member is inflated to provide form a seal between the blood vessel and the guide catheter and a vacuum is applied to the main lumen of the first elongate tubular member to cause retrograde blood flow and carry fluid into the main lumen of the evacuation sheath assembly.

19 Claims, 13 Drawing Sheets

U.S. PATENT DOCUMENTS

| | | | |
|---|---|---|---|
| 3,886,948 A | 6/1975 | Hakim | |
| 4,228,125 A | 10/1980 | Lobdell et al. | |
| 4,482,346 A | 11/1984 | Reinicke | |
| 4,655,746 A | 4/1987 | Daniels | |
| 4,696,668 A | 9/1987 | Wilcox | |
| 4,784,636 A | 11/1988 | Rydell | |
| 4,883,460 A | 11/1989 | Zanetti | |
| 4,917,667 A | 4/1990 | Jackson | |
| 4,921,478 A | 5/1990 | Solano | |
| 4,994,033 A | 2/1991 | Shockey et al. | |
| 5,011,488 A | 4/1991 | Ginsburg | |
| 5,019,041 A | 5/1991 | Robinson et al. | |
| 5,058,570 A | 10/1991 | Idemoto et al. | |
| 5,059,178 A | 10/1991 | Ya | |
| 5,074,845 A | 12/1991 | Miraki | |
| 5,108,414 A | 4/1992 | Enderle | |
| 5,137,013 A * | 8/1992 | Chiba et al. | 606/205 |
| 5,169,379 A * | 12/1992 | Freed et al. | 600/18 |
| 5,219,355 A | 6/1993 | Parodi | |
| 5,250,060 A | 10/1993 | Carbo | |
| 5,324,260 A | 6/1994 | O'Neill | |
| 5,350,395 A | 9/1994 | Yock | |
| 5,368,566 A | 11/1994 | Crocker | |
| 5,385,562 A | 1/1995 | Adams et al. | |
| 5,413,549 A | 5/1995 | Leschinsky | |
| 5,423,742 A | 6/1995 | Theron | |
| 5,451,207 A | 9/1995 | Yock | |
| 5,451,233 A | 9/1995 | Yock | |
| 5,453,099 A | 9/1995 | Lee | |
| 5,459,700 A | 10/1995 | Jacobs | |
| 5,465,733 A * | 11/1995 | Hinohara et al. | 600/585 |
| 5,466,222 A | 11/1995 | Ressemann | |
| 5,484,412 A | 1/1996 | Pierpont | |
| 5,486,192 A * | 1/1996 | Walinsky et al. | 606/194 |
| 5,527,292 A | 6/1996 | Adams | |
| 5,533,987 A | 7/1996 | Pray | |
| 5,536,242 A | 7/1996 | Willard | |
| 5,569,204 A | 10/1996 | Cramer | |
| 5,573,508 A | 11/1996 | Thornton | |
| 5,643,208 A | 7/1997 | Parodi | |
| 5,709,701 A | 1/1998 | Parodi | |
| 5,728,064 A | 3/1998 | Burns et al. | |
| 5,728,065 A * | 3/1998 | Follmer et al. | 604/96.01 |
| 5,738,652 A * | 4/1998 | Boyd et al. | 604/96.01 |
| 5,749,888 A | 5/1998 | Yock | |
| 5,755,704 A | 5/1998 | Lunn | |
| 5,769,868 A | 6/1998 | Yock | |
| 5,779,721 A | 7/1998 | Nash | |
| 5,785,685 A | 7/1998 | Kugler et al. | |
| 5,797,949 A | 8/1998 | Parodi | |
| 5,820,594 A * | 10/1998 | Fontirroche et al. | 604/165.01 |
| 5,820,595 A | 10/1998 | Parodi | |
| 5,833,644 A | 11/1998 | Zadno-Azizi | |
| 5,833,650 A | 11/1998 | Imran | |
| 5,843,022 A | 12/1998 | Willard | |
| 5,868,706 A | 2/1999 | Cox | |
| 5,879,361 A | 3/1999 | Nash | |
| 5,879,499 A * | 3/1999 | Corvi | 156/175 |
| 5,891,090 A | 4/1999 | Thornton | |
| 5,902,290 A * | 5/1999 | Peacock et al. | 604/526 |
| 5,913,842 A * | 6/1999 | Boyd et al. | 604/28 |
| 5,916,193 A | 6/1999 | Stevens et al. | |
| 5,938,672 A | 8/1999 | Nash | |
| 5,964,223 A | 10/1999 | Baran | |
| 5,971,938 A | 10/1999 | Hart | |
| 5,989,263 A | 11/1999 | Shmulewitz | |
| 5,997,558 A | 12/1999 | Nash | |
| 6,007,545 A | 12/1999 | Venturelli | |
| 6,013,085 A | 1/2000 | Howard | |
| 6,022,336 A | 2/2000 | Zadno-Azizi | |
| 6,030,362 A | 2/2000 | Boussignac | |
| 6,036,715 A | 3/2000 | Yock | |
| 6,042,605 A | 3/2000 | Martin | |
| 6,080,170 A | 6/2000 | Nash | |
| 6,098,405 A | 8/2000 | Miyata et al. | |
| 6,117,124 A | 9/2000 | Parodi | |
| 6,126,635 A | 10/2000 | Simpson | |
| 6,135,991 A | 10/2000 | Muni | |
| 6,146,370 A | 11/2000 | Barbut | |
| 6,152,909 A | 11/2000 | Bagaisan | |
| 6,156,005 A | 12/2000 | Theron | |
| 6,156,010 A | 12/2000 | Kuracina et al. | |
| 6,159,195 A | 12/2000 | Ha | |
| 6,165,158 A * | 12/2000 | Dutta | 604/265 |
| 6,176,844 B1 | 1/2001 | Lee | |
| 6,206,868 B1 | 3/2001 | Parodi | |
| 6,210,363 B1 * | 4/2001 | Esch et al. | 604/96.01 |
| 6,228,072 B1 | 5/2001 | Omaleki | |
| 6,231,588 B1 | 5/2001 | Zadno-Azizi | |
| 6,234,996 B1 | 5/2001 | Bagaoisan et al. | |
| 6,270,477 B1 | 8/2001 | Bagaoisan | |
| 6,295,989 B1 | 10/2001 | Connors, III | |
| 6,312,407 B1 | 11/2001 | Zadno-Azizi | |
| 6,355,016 B1 | 3/2002 | Bagaoisan | |
| 6,361,637 B2 | 3/2002 | Martin | |
| 6,398,773 B1 | 6/2002 | Bagaoisan | |
| 6,413,235 B1 | 7/2002 | Parodi | |
| 6,423,032 B2 | 7/2002 | Parodi | |
| 6,454,741 B1 | 9/2002 | Muni | |
| 6,485,500 B1 | 11/2002 | Kokish | |
| 6,497,670 B1 | 12/2002 | Parodi | |
| 6,517,515 B1 | 2/2003 | Eidenschink | |
| 6,520,986 B2 | 2/2003 | Martin | |
| 6,524,323 B1 | 2/2003 | Nash | |
| 6,533,800 B1 | 3/2003 | Barbut | |
| 6,540,712 B1 | 4/2003 | Parodi | |
| 6,544,276 B1 | 4/2003 | Azizi | |
| 6,569,147 B1 | 5/2003 | Evans | |
| 6,569,148 B2 | 5/2003 | Bagaoisan | |
| 6,582,396 B1 | 6/2003 | Parodi | |
| 6,589,264 B1 | 7/2003 | Barbut | |
| 6,592,546 B1 | 7/2003 | Barbut | |
| 6,592,557 B2 | 7/2003 | Barbut | |
| 6,595,980 B1 | 7/2003 | Barbut | |
| 6,605,074 B2 | 8/2003 | Zadno-Aziziz | |
| 6,605,102 B1 | 8/2003 | Mazzocchi | |
| 6,623,471 B1 | 9/2003 | Barbut | |
| 6,626,886 B1 | 9/2003 | Barbut | |
| 6,632,236 B2 | 10/2003 | Hogendijk | |
| 6,635,029 B1 | 10/2003 | Venturelli | |
| 6,635,046 B1 | 10/2003 | Barbut | |
| 6,645,222 B1 | 11/2003 | Parodi | |
| 6,652,480 B1 | 11/2003 | Imran | |
| 6,652,546 B1 | 11/2003 | Nash | |
| 6,652,565 B1 * | 11/2003 | Shimada et al. | 607/105 |
| 6,682,505 B2 | 1/2004 | Bates | |
| 6,682,543 B2 | 1/2004 | Barbut | |
| 6,712,806 B2 | 3/2004 | St. Germain | |
| 6,716,183 B2 | 4/2004 | Clayman et al. | |
| 6,733,474 B2 | 5/2004 | Kusleika | |
| 6,743,196 B2 | 6/2004 | Barbut | |
| 6,746,465 B2 * | 6/2004 | Diederich et al. | 606/192 |
| 6,786,888 B1 | 9/2004 | Zadno-Azizi | |
| 6,790,204 B2 | 9/2004 | Zadno-Azizi | |
| 6,793,667 B2 * | 9/2004 | Hebert et al. | 606/200 |
| 6,805,692 B2 | 10/2004 | Muni | |
| 6,811,550 B2 | 11/2004 | Holland et al. | |
| 6,827,701 B2 | 12/2004 | MacMahon | |
| 6,830,577 B2 | 12/2004 | Nash | |
| 6,830,579 B2 | 12/2004 | Barbut | |
| 6,837,881 B1 | 1/2005 | Barbut | |
| 6,840,949 B2 | 1/2005 | Barbut | |
| 6,843,797 B2 | 1/2005 | Nash | |
| 6,849,068 B1 | 2/2005 | Bagaoisan | |
| 6,855,136 B2 | 2/2005 | Dorros | |
| 6,878,128 B2 | 4/2005 | MacMahon | |
| 6,887,220 B2 | 5/2005 | Barbut | |
| 6,887,227 B1 | 5/2005 | Barbut | |
| 6,896,663 B2 | 5/2005 | Barbut | |
| 6,902,540 B2 | 6/2005 | Dorros | |
| 6,905,490 B2 | 6/2005 | Parodi | |
| 6,905,505 B2 | 6/2005 | Nash | |
| 6,908,474 B2 | 6/2005 | Hogendijk | |
| 6,936,056 B2 | 8/2005 | Nash | |
| 7,402,151 B2 * | 7/2008 | Rosenman et al. | 604/95.05 |
| 7,771,362 B2 * | 8/2010 | Williams et al. | 600/486 |
| 7,955,246 B2 * | 6/2011 | Lubock et al. | 600/3 |

| | | |
|---|---|---|
| 2001/0012951 A1 | 8/2001 | Bates |
| 2001/0037085 A1 | 11/2001 | Euteneuer |
| 2001/0044598 A1 | 11/2001 | Parodi |
| 2001/0047184 A1 | 11/2001 | Connors, III |
| 2001/0049550 A1 | 12/2001 | Martin |
| 2002/0002397 A1 | 1/2002 | Martin |
| 2002/0016564 A1 | 2/2002 | Courtney |
| 2002/0016565 A1 | 2/2002 | Zadno-Azizi |
| 2002/0022859 A1 | 2/2002 | Hogendijk |
| 2002/0026145 A1 | 2/2002 | Bagaoisan |
| 2002/0029031 A1 | 3/2002 | Bagaoisan |
| 2002/0035347 A1 | 3/2002 | Bagaoisan |
| 2002/0052638 A1 | 5/2002 | Zadno-Azizi |
| 2002/0062119 A1 | 5/2002 | Zadno-Azizi |
| 2002/0065507 A1 | 5/2002 | Zadno-Azizi |
| 2002/0087119 A1 | 7/2002 | Parodi |
| 2002/0091407 A1 | 7/2002 | Zadno-Azizi |
| 2002/0107479 A1 | 8/2002 | Bates |
| 2002/0151922 A1 | 10/2002 | Hogendijk |
| 2002/0161395 A1 | 10/2002 | Douk |
| 2002/0173815 A1 | 11/2002 | Hogendijk |
| 2002/0177800 A1 | 11/2002 | Bagaoisan |
| 2002/0188314 A1 | 12/2002 | Anderson |
| 2003/0009146 A1 | 1/2003 | Muni |
| 2003/0023200 A1 | 1/2003 | Barbut |
| 2003/0023204 A1 | 1/2003 | Vo |
| 2003/0023227 A1 | 1/2003 | Zadno-Azizi |
| 2003/0040694 A1 | 2/2003 | Dorros |
| 2003/0040704 A1 | 2/2003 | Dorros |
| 2003/0040705 A1 | 2/2003 | Dorros |
| 2003/0040762 A1 | 2/2003 | Dorros |
| 2003/0055398 A1 | 3/2003 | Imran |
| 2003/0069549 A1 | 4/2003 | MacMahon |
| 2003/0083617 A1 | 5/2003 | St. Germain |
| 2003/0097036 A1 | 5/2003 | St. Germain |
| 2003/0150821 A1 | 8/2003 | Bates |
| 2003/0158518 A1 | 8/2003 | Schonholz |
| 2003/0171769 A1 | 9/2003 | Barbut |
| 2003/0171770 A1 | 9/2003 | Kusleika |
| 2003/0171771 A1 | 9/2003 | Anderson |
| 2003/0187390 A1 | 10/2003 | Bates |
| 2003/0187391 A1 | 10/2003 | Hogendijk |
| 2003/0187392 A1 | 10/2003 | Hogendijk |
| 2003/0191434 A1 | 10/2003 | Dorros |
| 2003/0208222 A1 | 11/2003 | Zadno-Azizi |
| 2003/0233117 A1 | 12/2003 | Adams |
| 2004/0010280 A1 | 1/2004 | Adams |
| 2004/0010282 A1 | 1/2004 | Kusleika |
| 2004/0015150 A1 | 1/2004 | Zadno-Azizi |
| 2004/0019310 A1 | 1/2004 | Hogendijk |
| 2004/0034366 A1 | 2/2004 | van der Burg |
| 2004/0054347 A1 | 3/2004 | Zadno-Azizi |
| 2004/0054348 A1 | 3/2004 | Hogendijk |
| 2004/0064092 A1 | 4/2004 | Tsugita |
| 2004/0069549 A1 | 4/2004 | MacMahon |
| 2004/0092869 A1 | 5/2004 | Venturelli |
| 2004/0127885 A1 | 7/2004 | Barbut |
| 2004/0193099 A1 | 9/2004 | MacMahon |
| 2004/0260239 A1 | 12/2004 | Kusleika |
| 2005/0004517 A1 | 1/2005 | Courtney |
| 2005/0004594 A1 | 1/2005 | Nool |
| 2005/0010247 A1 | 1/2005 | Kusleika |
| 2005/0020973 A1 | 1/2005 | MacMahon |
| 2005/0085769 A1 | 4/2005 | MacMahon |
| 2005/0090854 A1 | 4/2005 | Barbut |
| 2005/0124849 A1 | 6/2005 | Barbut |
| 2005/0124973 A1 | 6/2005 | Dorros |
| 2005/0131453 A1 | 6/2005 | Parodi |
| 2005/0149112 A1 | 7/2005 | Barbut |
| 2005/0154298 A1 | 7/2005 | Barbut |
| 2005/0159640 A1 | 7/2005 | Barbut |

FOREIGN PATENT DOCUMENTS

| | | |
|---|---|---|
| WO | WO 9742879 | 11/1997 |
| WO | WO 9744082 | 11/1997 |
| WO | WO 9838929 | 9/1998 |
| WO | WO 9838930 | 9/1998 |
| WO | WO 9839046 | 9/1998 |
| WO | WO 9839047 | 9/1998 |
| WO | WO 99/08744 | 2/1999 |
| WO | WO 9942059 | 8/1999 |
| WO | WO 9942157 | 8/1999 |
| WO | WO 9945835 | 9/1999 |
| WO | WO 0007657 | 2/2000 |
| WO | WO 0044429 | 8/2000 |
| WO | WO 0051675 | 9/2000 |
| WO | WO 0054673 | 9/2000 |
| WO | WO 0056391 | 9/2000 |
| WO | WO 00/76390 | 12/2000 |
| WO | WO 0076390 | 12/2000 |
| WO | WO 0105329 | 1/2001 |
| WO | WO 0112104 | 2/2001 |
| WO | WO 0145590 | 6/2001 |
| WO | WO 0145592 | 6/2001 |
| WO | WO 0158382 | 8/2001 |
| WO | WO 0170326 | 9/2001 |
| WO | WO 0191844 | 12/2001 |
| WO | WO 0222199 | 3/2002 |
| WO | WO 0232495 | 4/2002 |
| WO | WO 03007797 | 1/2003 |
| WO | WO 03008015 | 1/2003 |
| WO | WO 03009880 | 2/2003 |
| WO | WO 2004002564 | 1/2004 |
| WO | WO 2004011058 | 2/2004 |

OTHER PUBLICATIONS

Kachel, Reiner, M.D., "Results of Balloon Angioplasty in the Carotid Arteries," J. Endovasc. Surg., 1996 3:22-30.

Kachel, R., "Current Status and Future Possibilities of Balloon Angioplasty in the Carotid Artery," Connors, Wojak (Eds); *Interventional Neuroradiology Strategies and Pratical Techniques*, Chapter 46, pp. 473-484, 1998.

Kinney, Thomas B., et al., "Shear Force in Angioplasty: Its Relation to Catheter Design and Function," American Journal of Roentology, Jan. 1985, pp. 115-122.

Kinoshita, Akira, et al., "Percutaneous Transluminal Angioplasty of Internal Carotid Artery: A Preliminary Report of Seesaw Balloom Technique," Neurological Research, 1993.

McCleary, A.J., et al., "Cerebral Haemodynamics and Embolization During Carotid Angioplasty in High-Risk Patients," The British Journal of Surgery, vol. 85, No. 6, Jun. 1988, pp. 771-774.

Soler-Singla, L., et al., "Angioplastia Carotidea Con Proteccion Cerebral Y Protesis Endovascular," Revista De Neurologia, 1997; vol. 25, No. 138, pp. 287-290.

Tanaka, Masato, et al., "Percutaneous Transluminal Angioplasty (PTA) for Stenosis at the Subclavian Artery and at the Origin of the Vertebral Artery: Therapeutic indication and some adjunctive safe methods during the PTA," Neuorogical Surgery, vol. 22 No. 10, 1994, pp. 939-946.

Terada, Tomoaki, et al., "Newly Developed Blocking Balloon Catherter for PTA of Internal Cartoid Atery," Neurological Surgery, vol. 21, No. 10, 1993, pp. 891-895.

Theron, Jacques, "Angioplasty of Brachiocephalic Vessels," Interventional Neuroradiology Endovascular Therapy of the Central Nervous System, Chapter 13, 1992, pp. 167-180.

Theron, Jacques G., MD, "Carotid Artery Stenosis: Treatment with Protected Balloon Angioplasty and Stent Placement," Radiology, vol. 201 No. 3, Decembr 1996, pp. 627-633.

Theron, Jacques, MD, "Cerebral Protection During Carotid Angioplasty," Letters to the Editors, J. Endovasc. Surg., 1996:3:484-486.

Theron, J. et al., "New Triple Coaxial Catheter System for Carotid Angioplasty with Cerebral Protection," American Journal of Neuroradiology, Sep. 1990, pp. 869-874.

* cited by examiner

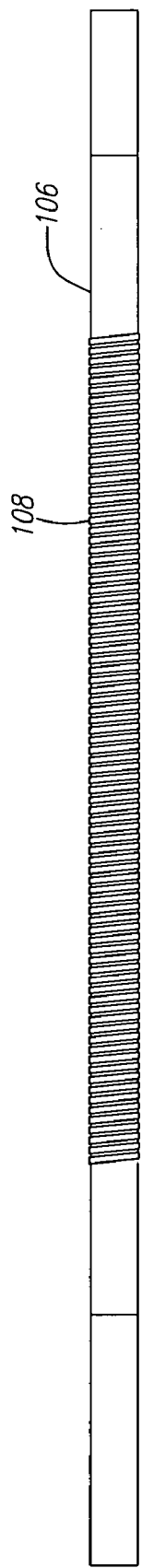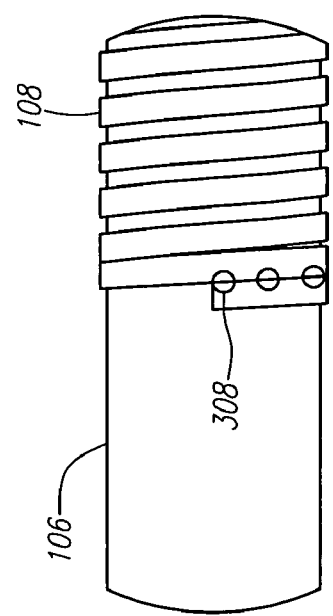
FIG. 3A
FIG. 3B

EMBOLIC PROTECTION DEVICE AND METHODS OF USE

FIELD OF THE INVENTION

The present invention relates to apparatus and methods used to prevent the introduction of emboli into the bloodstream during and after surgery performed to reduce or remove blockage in blood vessels.

BACKGROUND OF THE INVENTION

Narrowing or occlusion of blood vessels, such as the walls of an artery, inhibits normal blood flow. Such blockages, whether partial or full, can have serious medical consequences, depending upon their location within a patient's vascular system. Narrowing or blockage of the coronary vessels that supply blood to the heart, a condition known as atherosclerosis, may cause damage to the heart. Heart attacks (myocardial infarction) may also result from this condition. Other vessels are also prone to narrowing, including carotids, renals, cerebrals, and other peripheral arteries.

Various surgical procedures are currently used to reduce or remove the blockage in blood vessels. Such procedures include balloon angioplasty, which involves inserting a balloon catheter into the narrowed or occluded area, expanding the balloon in the narrow or occluded area, and if necessary, placing a stent in the now expanded area to keep it open. Another common procedure used is atherectomy where the lesion is cut away and removed from the vessel, or abrasively ground, sending the small particulates downstream. Other endovascular procedures make use of thrombectomy, drug delivery, radiation, stent-grafts, and various diagnostic devices.

Another alternative is bypass surgery in which a section of vein is removed from, for example, the patient's leg, e.g., a saphenous vein, to be used as a graft to form a pathway to bypass the occluded area. The saphenous vein graft (SVG), however, is also susceptible to becoming occluded in a manner similar to that of the bypassed vessel. In such a case, angioplasty (with or without the use of a stent) or atherectomy is often used on the SVG to remove or reduce the blockage.

Each of the above described procedures carries with it the risk that some of the treated plaque, or other obstructive material such as thrombus, will be disrupted, resulting in embolic particulates released in the bloodstream. These emboli, if allowed to flow through the vascular system, may cause subsequent infarctions or ischemia in the patient. SVGs treated by angioplasty or atherectomy carry a particularly high risk of this result, but such problems are also encountered in the other types of procedures mentioned, such as carotids, or native coronary arteries, particularly those whose lesions include thrombus, such as those associated with acute myocardial infarction (AMI).

Several systems to prevent emboli being released into the bloodstream during such procedures have been tried. One system uses a balloon to totally occlude the artery distal (downstream) to the area of blockage to be treated. In this system, a guide wire with a balloon is introduced into the narrowed or occluded area, and passes through the narrowed or occluded area to a position downstream of the blockage. The balloon is inflated, the blockage is reduced or removed, and then the blood proximal to the balloon is withdrawn from the blood vessel to remove any particles or emboli which have resulted from the reduction of the blockage. While this system has shown a decrease in emboli related complications in patients undergoing such treatments, the event rate remains significant. One particular problem with this system is passing the guidewire and balloon through the narrowed or occluded area prior to occlusion with the balloon, creating the risk that emboli will be produced as the balloon passes through the blockage. Thus, any particulate or plaque disturbed during this passage which forms emboli prior to inflation of the balloon is free to flow through the vascular system, increasing the risk for infarction or ischemia. Also, any debris or embolic particulate matter which gathers around the edges of the balloon may slip downstream during deflation and retrieval of the balloon. In addition, this system requires that blood flow be totally occluded in the vessel for relatively prolonged intervals that may induce adverse cardiac events. Although this may not be a problem clinically, many patients perceive the occlusion of blood flow for this period of time as problematic.

Another system used to prevent emboli being released into the bloodstream during surgical intervention is a filter. As with the occlusion balloon, the filter must pass through the narrowed or occluded area and is deployed distal (downstream) to the blockage. The filter then catches any particulate material generated during the removal of the blockage. The filter offers the benefit that blood flow is not totally occluded. However, because the filter must pass through the blockage, it suffers from the same drawback as the previous system—risk of the creation of emboli during passage of the filter through the blockage. In addition, it is difficult to deploy the filter securely against the walls of the vessel to prevent flow around the filter and any debris or particulate matter which gathers around the edges of the filter may slip downstream during its retrieval. Also, in order to allow blood flow during the procedure, the pores of the filter should be at least 100 microns in diameter. The majority of emboli have a diameter between about 40 microns and about 100 microns. Thus, the filter will not catch the majority of emboli, which may flow downstream and cause an infarction or ischemia. The filter also cannot prevent the passage of certain neurohumoral or vasoactive substances which are released into the blood during the procedure and may contribute to generalized vasospasm of the distal coronary tree.

Thus, there is a need for an improved system and method of treating occluded vessels which can reduce the risk of distal embolization during vascular interventions. There is also a need for a system which reduces the amount of time that total occlusion of the blood flow is necessary.

SUMMARY OF THE INVENTION

In accordance with the invention, methods and apparatuses for reducing or removing a blockage within a vessel without permitting embolization of particulate matter are provided. The methods and apparatuses occlude blood flow for a minimal amount of time and capture particulate matter created during each step of the surgical process.

According to one aspect of the present invention, an evacuation sheath assembly is provided. The evacuation sheath assembly includes a first elongate tubular member having main lumen, wherein the main lumen is configured to be placed in fluid communication with the blood stream so that embolic particulate matter may be evacuated, contrast, saline or other therapeutic fluid may be infused or interventional devices may be delivered to a blood vessel. The evacuation sheath further includes an expandable sealing member configured to form a seal with a blood vessel and a second elongate tubular member with distal and proximal ends and an inflation lumen extending therebetween, wherein the inflation lumen is configured to be placed in fluid communication with the expandable member at the distal end. The evacuation sheath further includes gas inflator having a pressure regulating mechanism, wherein the gas inflator is configured to be connected to the proximal end of the inflation lumen to deliver provide a regulated pressure gas source for inflating the expandable member. The expandable member may be a balloon, alternatively the expandable member may be any suitable expandable sealing member.

In an alternative embodiment, the evacuation sheath assembly may further include a soft tip mounted on the distal end of the first elongate tubular member. Such a soft tip may further be secured to the distal end of first elongate tubular member and the distal end of the expandable member in order to provide a flexible, conical shape capable of can deforming and dilating to facilitate folding up a "winged out" balloon of an interventional device as it is withdrawn back through the main lumen of the evacuation sheath.

In an alternate embodiment, the first elongate tubular member may further be surrounded by a kink resistant structure, for example a kink resistant braid or a kink resistant coil. The kink resistant coil may be comprised of a ribbon wire and may have further be secured at the proximal and distal ends of the coil to prevent uncoiling by one or more laser welds joining one or more adjacent turns of the coil. In such an embodiment, the second elongate tubular member may then be secured to the first elongate member by mounting the second elongate tubular member to the kink resistant structure.

In addition, it is further contemplated that the second elongate tubular member and the first elongate tubular member surrounded by the kink resistant coil may further be enclosed by an encapsulation layer. The encapsulation layer may be made of PEBAX or another suitable material. The encapsulation layer may then be melted down to conform and bond to the surfaces of the first and second elongate members. In such a manner a single, flexible, multi-lumen tube comprising a main lumen and an inflation lumen may be formed.

According to another aspect of the present invention, the evacuation sheath may be sized to have an outer diameter substantially the same size as the inner diameter of a guide catheter, such as a 6 French guide catheter, alternatively a 7 French guide catheter, alternatively an 8 French guide catheter or any other size guide catheter. In an alternative embodiment, the outer diameter of the evacuation sheath may be covered with a lubricious coating. Additionally, the expandable member of evacuation assembly may also be covered with a lubricious coating.

According to another aspect of the present invention, the evacuation sheath assembly may further include a third elongate tubular member slidably insertable through the main lumen of the first elongate tubular member and extendable from the aperture of the main lumen for positioning beyond the distal end of the main lumen, wherein the third elongate tubular member has a proximal end, a distal end, a lumen extending therebetween. The lumen of the third elongate member further includes an aperture disposed at the distal end for communicating said lumen with the bloodstream and is connected at the proximal end of the tube with an infusion means for delivering a fluid into the blood stream.

According to another aspect of the present invention, a gas inflator for inflating and deflating the expandable member is provided. The gas inflator includes a shuttle mechanism for delivering a bolus of gas to an expandable member via an inflation lumen having one or more outlet ports in communication with the inflation lumen and a high pressure gas source having an inlet port in fluid communication with the shuttle mechanism. The gas inflator may further include a housing and one or more control switches on the housing for controlling gas flow within the inflation lumen, for example an inflation and a deflation button operably connected to the shuttle mechanism. In an alternative embodiment, the gas inflator may further include a mechanism for removing gas from the expandable member, which also may be connected to one or more control switches within the housing. In addition, the gas inflator may further include a tube operably sized to connect with the proximal end of an inflation lumen and place the inflation lumen in fluid communication with the one or more outlet ports.

According to another aspect of the present invention, the gas inflator may further comprise a puncturing mechanism connected to the high pressure gas cartridge, having a puncture spear and a lever for engaging the puncture spear. The high pressure gas cartridge contains a suitable high pressure gas for inflating the expandable member, for example Carbon Dioxide, Nitrous Dioxide or Helium. Additionally, the gas inflator may further comprises an in line filter for sterilizing the gas before delivery to the inflation lumen.

According to another aspect of the present invention, a shuttle mechanism of the gas inflator may be operably connected to inflation and deflation buttons on the housing and may further include a cylindrical shuttle chamber in fluid communication with the one or more outlet ports and the high pressure gas source, wherein a series of seals, for example o-ring seals, are mounted on the shuttle and spaced apart to divide the shuttle chamber into a pressure chamber and a vacuum chamber, wherein the vacuum chamber has a one way bypass seal for venting gas from the vacuum chamber, and a vacuum piston operably connected to the one way bypass seal of the vacuum chamber. The shuttle mechanism further includes translation output connected to the inflation and deflation buttons for moving the shuttle longitudinally within the shuttle chamber to alternately place the vacuum and pressure chambers in fluid communication with a shuttle chamber outlet port and the pressure chamber in fluid communication with a high pressure gas source. In addition, the pressure chamber may further comprise an inlet port in fluid contact with the high pressure gas source for filling the pressure chamber with a bolus of gas. Additionally, the shuttle mechanism may further comprise both a high pressure resistance outlet port and a low pressure resistance outlet port.

In an alternative embodiment, the vacuum chamber may be formed by one o-ring seal and the one-way venting seal spaced apart to define a chamber and the pressure chamber is formed by two or more o-ring seals spaced apart to define a chamber.

In an alternative embodiment, the gas inflator may further comprises a venting system for regulating the pressure of the gas delivered to inflation lumen from the outlet port. Such a venting system may include at least one pressure relief valve for maintaining a constant delivery pressure to the inflation lumen. Alternatively, the venting system may comprise a second pressure release valve. The pressure relief valves may be spring-loaded poppet valves. In addition, one of the pressure relief valves may further comprises a pressure indicator in fluid communication with the inflation lumen, wherein the housing further comprises a window for viewing the pressure indicator.

According to another aspect of the invention, a method for treating a diseased blood vessel is provided. The method includes advancing an elongate tubular member into the blood vessel through the lumen of the guide catheter, positioning the elongate tubular member within the diseased blood vessel, inflating the expandable sealing member located on the distal end of the of the elongate tubular member to form a seal between the region of interest of the diseased blood vessel and the distal end of the guide catheter; and applying a vacuum to the elongate tubular member to cause retrograde blood flow in the blood vessel and to carry fluid into the lumen of the elongate tubular member.

According to another aspect of the invention, a method for treating a diseased blood vessel is provided. The method includes advancing an elongate tubular member into the blood vessel through the lumen of the guide catheter, positioning the elongate tubular member within the diseased blood vessel, inflating the expandable sealing member located on the distal end of the of the elongate tubular member to occlude normal ante grade blood flow in the blood vessel proximal to the region of interest, and applying a vacuum to the elongate tubular member to cause retrograde blood flow in the blood vessel and to carry fluid into the lumen of the elongate tubular member. In addition, the method may further include the step of removing the elongate tubular member from the blood vessel.

According to another aspect of the invention, a method for treating a diseased blood vessel is provided. The method includes advancing a guide catheter proximal to the blood vessel, advancing an elongate tubular member into the blood vessel through the lumen of the guide catheter and beyond the distal opening, wherein the proximal end of the elongate tubular member extends proximally outside the patient during use, positioning the elongate tubular member within the diseased blood vessel, inflating the expandable sealing member located on the distal end of the of the elongate tubular member to occlude normal ante grade blood flow in the blood vessel proximal to the region of interest, and applying a vacuum to the elongate tubular member to cause retrograde blood flow in the blood vessel and to carry fluid into the lumen of the elongate tubular member.

In addition, the method of treating a blood vessel may further include the steps of advancing an infusion catheter through the evacuation lumen and introducing fluid into the blood stream via the infusion catheter while the expandable member is inflated.

In another alternative embodiment, the method of treating a blood vessel may further include the steps of injecting contrast dye through the lumen of the elongate tubular member to verify the occlusion of the blood vessel.

In addition the method of treating a blood vessel may further include the step of applying a second vacuum to the evacuation sheath assembly to re-initiate retrograde flow in the blood vessel and to carry remaining embolic material from the blood vessel into the lumen of the elongate tubular member. In another embodiment, the method may further include the step of applying a vacuum to the gas inflator to deflate the expandable member.

According to another aspect of the present invention the step of inflating the expandable member may further comprises the steps of puncturing a high pressure gas cartridge within the gas inflator, filling a pressure chamber in the gas inflator with a bolus of high pressure gas, depressing a pressure button on the gas inflator to advance a shuttle in the gas inflator, wherein the shuttle transports the pressure chamber into communication with a high pressure resistance output port and wherein the high pressure resistance output port is in communication with the inflation lumen via a tube extending from the gas inflator, regulating the flow of the high pressure gas from the high pressure resistance output port via at least one pressure relief valve, and delivering a low pressure volume of gas to the tube in communication with the inflation lumen and thereby inflating the expandable member.

In an alternative embodiment, the step of inflating the expandable member may also include the step of priming the inflation lumen to remove the ambient air from the inflation lumen and the expandable member prior to advancing the evacuation assembly through the guide catheter. Priming the inflation lumen may further comprise the steps of activating a piston in the gas inflator, wherein the piston in operably connected to a seal with a one way bypass which defines the opening of a vacuum chamber in the gas inflator, releasing the piston and creating a vacuum in a vacuum chamber, depressing a vacuum button on the gas inflator to advance a shuttle mechanism within the gas inflator and place the vacuum chamber in fluid communication with a low pressure resistance output port wherein the low pressure resistance output port is in communication with the inflation lumen, and suctioning the gas from the inflation lumen and the expandable member via the low resistance valve output.

According to another aspect of the present invention the step of deflating the expandable member may further include activating a piston in the gas inflator, wherein the piston in operably connected to a seal with a one way bypass which defines the opening of a vacuum chamber in the gas inflator, releasing the piston and creating a vacuum a vacuum chamber, depressing a vacuum button on the gas inflator to advance a shuttle mechanism within the gas inflator and place the vacuum chamber in fluid communication with a low pressure resistance output port wherein the low pressure resistance output port is in communication with the inflation lumen, suctioning the gas from the inflation lumen and the expandable member via the low resistance valve output.

In an alternative embodiment, the pressure in the inflation lumen may be monitored as the expandable member is being inflated and/or deflated.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 3A illustrates an embodiment of a kink resistant coil for use in the present invention.

FIG. 3B illustrates an embodiment of welds for use in securing a kink resistant coil to the elongate tubular member of a device according to the present invention.

DETAILED DESCRIPTION OF THE INVENTION

The present invention provides a system and method for evacuating emboli, particulate matter and other debris from a blood vessel, and particularly from an occluded blood vessel. As used herein, an "occlusion," "blockage," or "stenosis" refers to both complete and partial blockages of the vessels, stenoses, emboli, thrombi, plaque, debris and any other particulate matter which at least partially occludes the lumen of the blood vessel.

This method and apparatus are particularly suited to be used in diseased blood vessels that have particularly fragile lesions, or vessels whereby the consequences of even small numbers of small emboli may be clinically significant. Such blood vessels include diseased SVGs, carotid arteries, coronary arteries with thrombus such as associated with AMI, and renal arteries. However, it is contemplated that the method and apparatus may also be applied to peripheral, neuro, and other vascular and non-vascular applications.

Figure 1A:
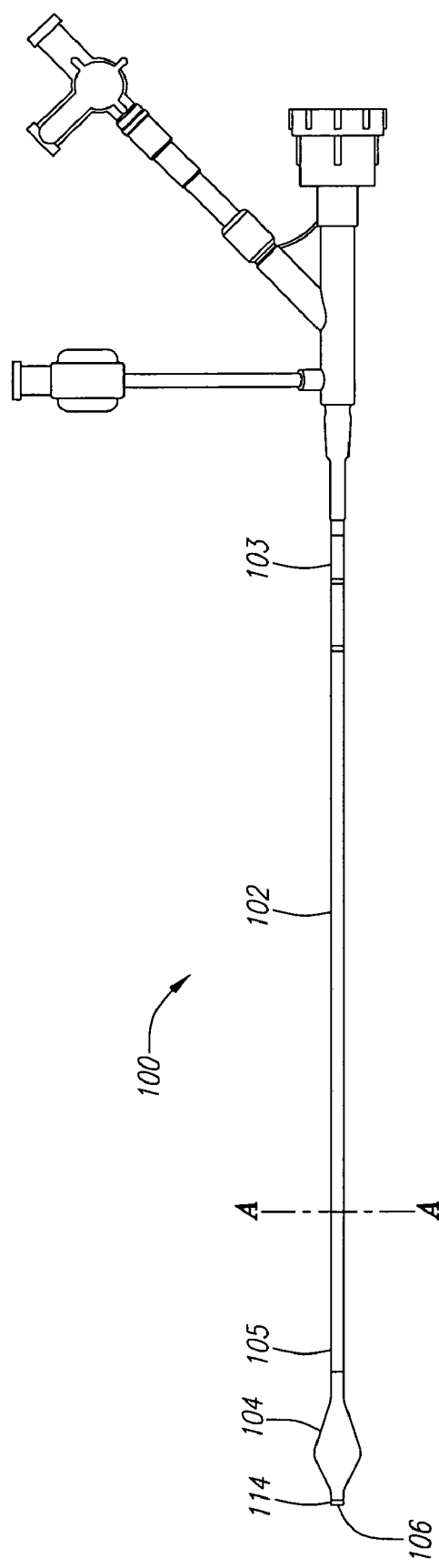
FIG. 1A is a side view of an embodiment of a full length evacuation sheath according to the present invention.
Figure 1B:
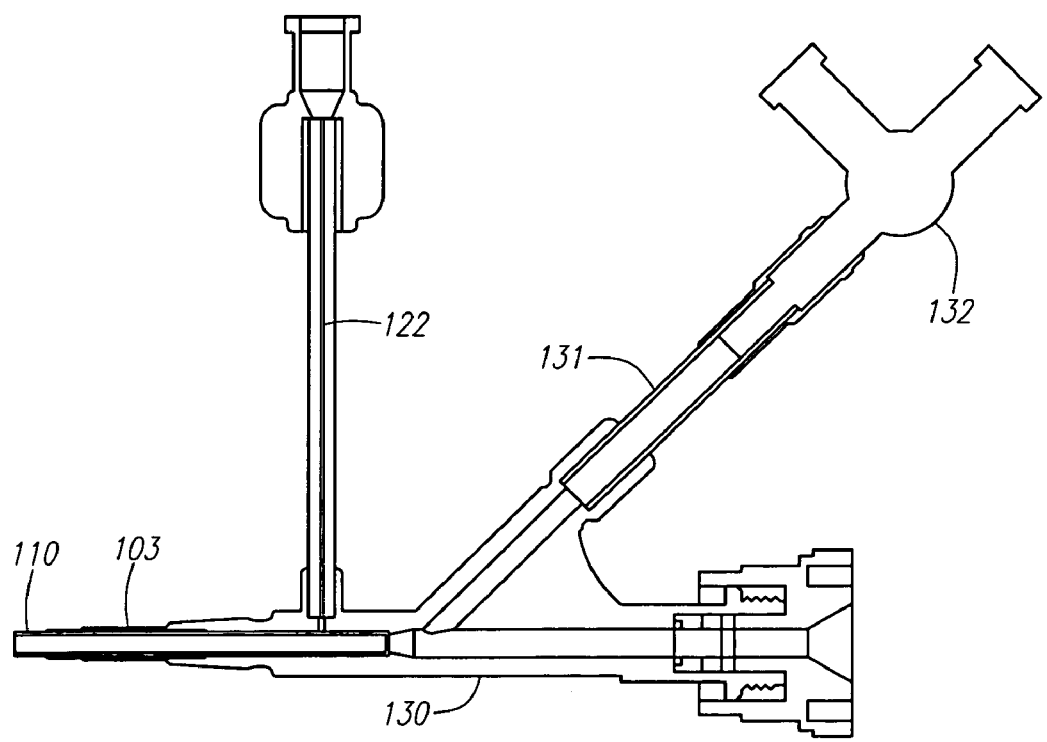
FIG. 1B is a side view of the proximal end of an embodiment of a full length evacuation sheath according to the present invention.
Figure 1C:
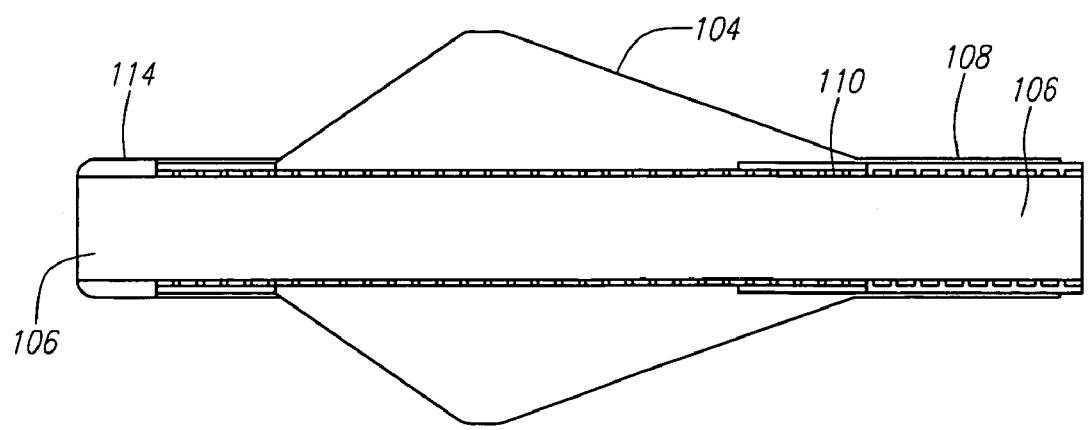
FIG. 1C is a side view of the distal end of an embodiment of a full length evacuation sheath according to the present invention.
Figure 1D:
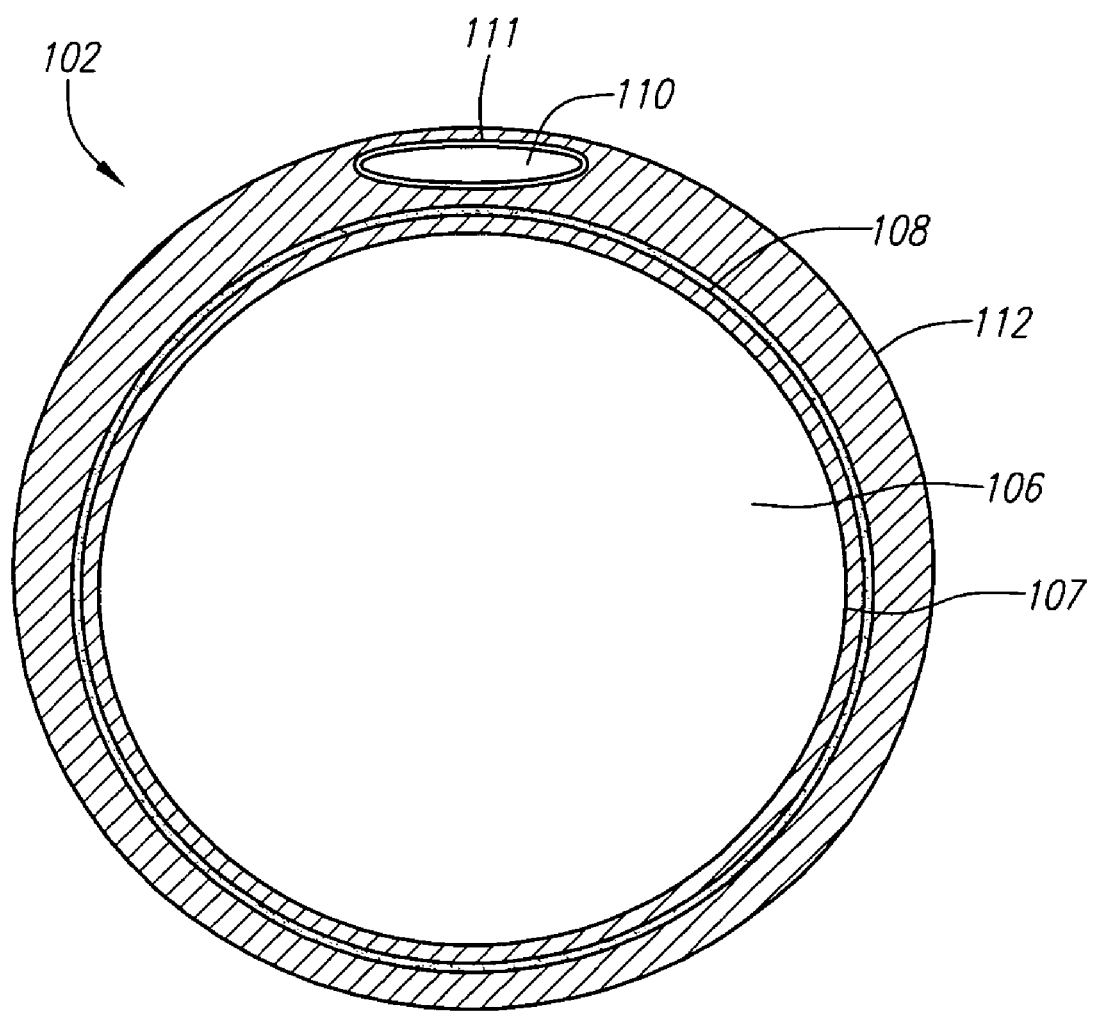
FIG. 1D illustrates a cross sectional view of an embodiment of a full length evacuation sheath taken along plane A-A according to the present invention.

FIG. 1A illustrates an embodiment of an evacuation sheath assembly 100. As shown, the evacuation sheath assembly 100 includes a multi-lumen elongate tubular member 102 having a main lumen 106 extending essentially the full length of the elongate tubular member 102 and an expandable member 104 mounted at the distal end 105 of the elongate tubular member. As shown in FIGS. 1B, 1C and 1D, the multi-lumen elongate tubular member 102 further includes an inflation lumen 110 (most easily seen in FIGS. 1C and 1D) connected at the proximal end 103 to a gas inflator 120 (shown in FIG. 2) and extending distally to connect with the expandable member 104 mounted at the distal end 105 of the elongate tubular member 102. The evacuation sheath assembly further includes a soft tip 114 at the distal end and is connected to a manifold 130 at the proximal end.

As shown in FIG. 1B, the manifold includes an inflation connector tube 122, which when connected to the inflation system (not shown) defines a pathway for inflation of the expandable member 104 via an inflation lumen 110 in the multi-lumen elongate tubular member 102. The manifold includes an aspiration tube 131, which is in fluid communication with the evacuation lumen 106. A stopcock 132 is preferably connected to the aspiration tube 130, which facilitates the use of the main lumen 106 for evacuation of embolic particulate matter and/or infusion of fluids there through to the vasculature. In use, as depicted in FIG. 2, the aspiration tube 131 and stopcock 132 may be connected to both an evacuation syringe 210 which would be alternately used to draw the embolic particulate matter from the main lumen and an inflation syringe 211 which would alternately be used to deliver fluids, for example radiopaque contrast agent for angiography, saline or therapeutic agents through the main lumen 106.

Figure 1E:
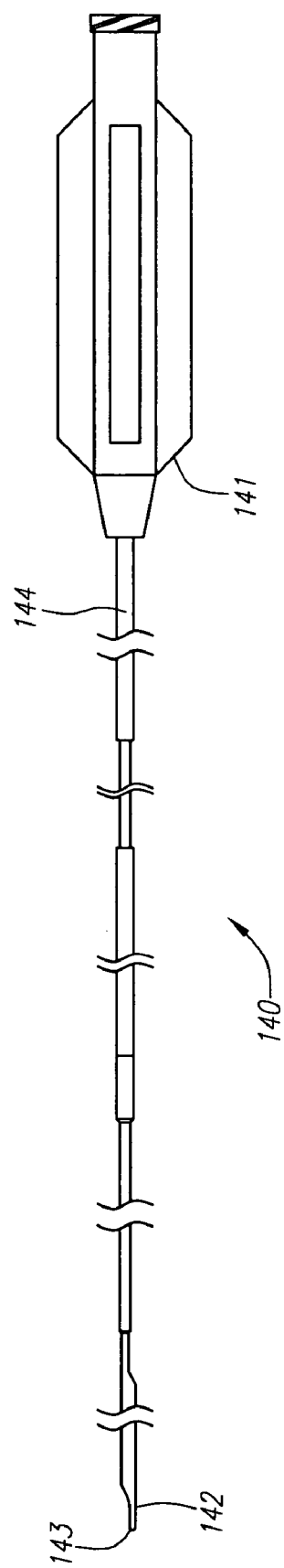
FIG. 1E illustrates a side view of an embodiment of a third elongate tubular member for use in an alternate embodiment of an evacuation sheath according to the present invention.

In an alternative embodiment, the evacuation sheath assembly may include a third elongate tubular member 140, as depicted in FIG. 1E, slidably insertable through the main lumen and extendable from the aperture of the main lumen for positioning beyond the distal end of the main lumen. In this embodiment, the third elongate tubular member 140 has a proximal end 141, a distal end 142, a lumen 144 extending therebetween, and an aperture 143 disposed at the distal end for communicating said lumen 144 with the bloodstream. In use, the third elongate tubular member may be delivered to a blood vessel through the main lumen of the multi-lumen tube so that the distal end of the lumen is in fluid communication with the blood stream. The proximal end of the third elongate tubular member may then be connected at the with an inflation syringe or other infusion means for delivering a fluid such as saline or another therapeutic fluid into the blood stream.

Figure 2:
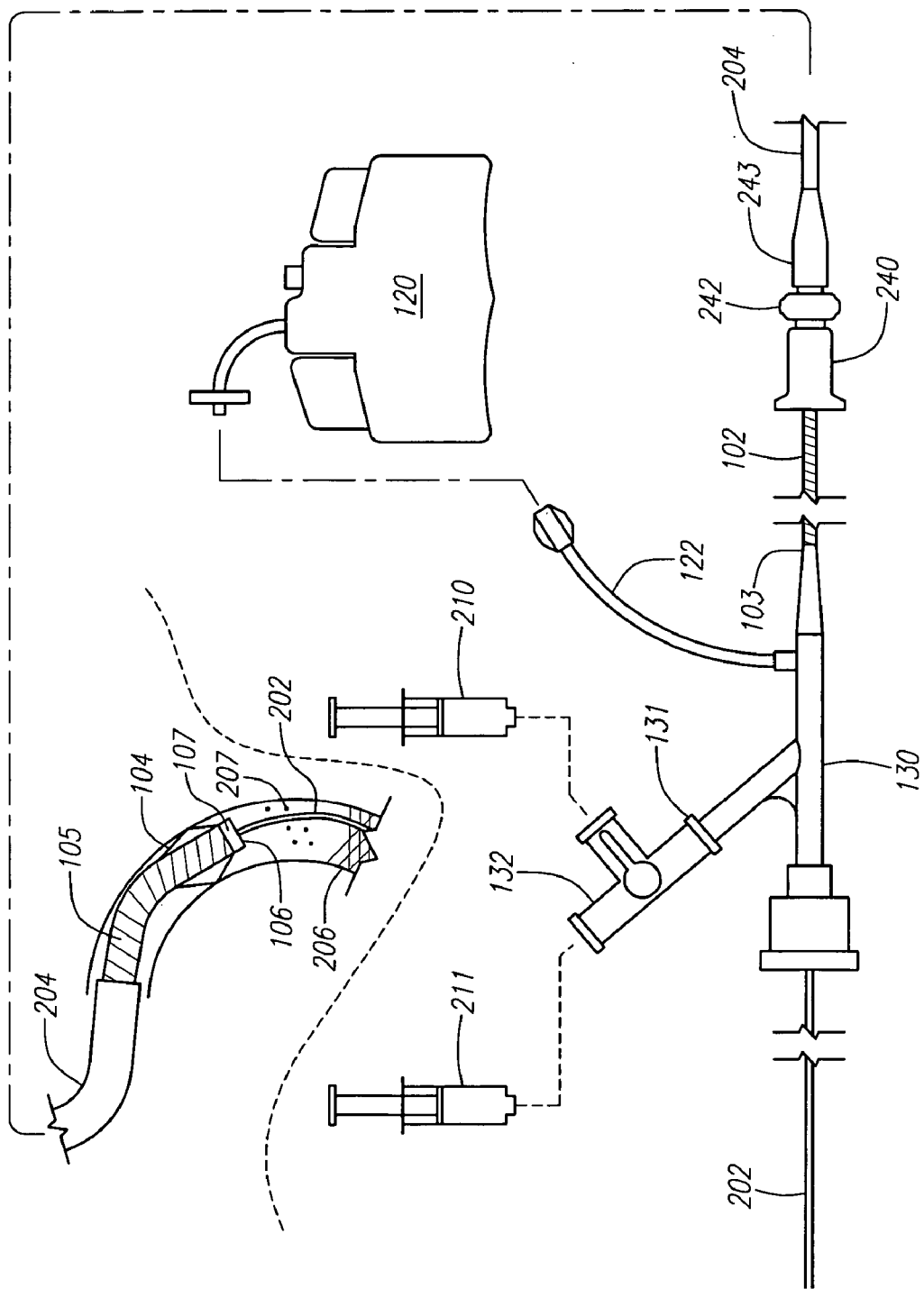
FIG. 2 illustrates a schematic diagram of an embodiment of the device in use according to the present invention.
Figure 4:
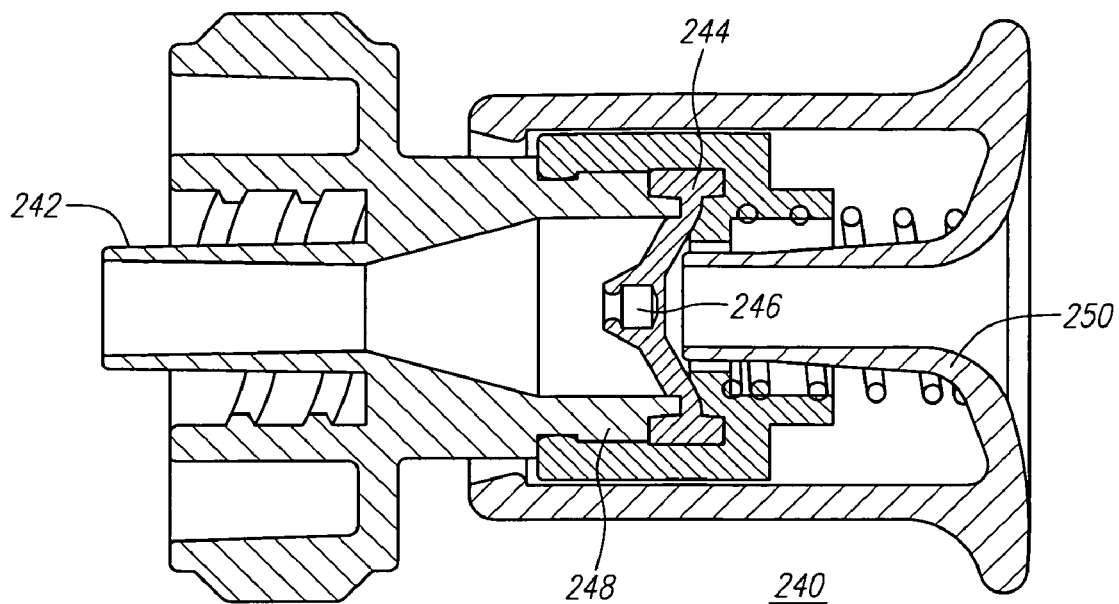
FIG. 4 illustrates an embodiment of a sealing mechanism for use in the present invention.

As shown in FIG. 2, the proximal end of the evacuation sheath assembly 100 may be used with a lip seal 240 for isolating fluid communication between the multi-lumen elongate tubular member 102 and the guide catheter 204. The distal end of the lip seal 240 includes a male luer fitting 242 which connects to the female luer fitting 243 at the proximal end of the guide catheter 204. FIG. 4 shows an embodiment of a lip seal according to this invention in more detail. The lip seal 240 includes a diaphragm 244 with an opening 246 operably sized to allow passage of the multi-lumen elongate tubular member 102 therethrough, a stationary base 248, a tubular actuator 250 and a male luer adaptor 242 at the distal end for securing to a female luer fitting at the proximal end of a guide catheter. In use, when the actuator 250 is depressed, it pushes the diaphragm 244 against the stationary base 248 and causes the opening 246 in the diaphragm to expand. While the opening 246 is expanded, the multi-lumen elongate tubular member 102 can easily be slid through the tubular actuator 250, and diaphragm opening 246, and into the lumen of the guide catheter 204. Once the actuator 250 is released, the opening in the diaphragm 244 retracts, forming a seal around the multi-lumen elongate tubular member 102 and isolating fluid communication from the guide catheter, to prevent back-bleeding out of the guide catheter 204, or to prevent air ingress into the lumen of the guide catheter 204. Since the evacuation lumen in the multi-lumen elongate tubular member 102 may be used for delivery of interventional catheters, or fluids such as saline, contrast dyes or therapeutic agents, it is possible to completely isolate the guide catheter from fluid communication with the manifold of the evacuation sheath assembly 100. As shown in FIG. 2, once the elongate tubular member 102 is inserted in the lip seal 240, the main lumen 106 becomes the lumen through which particulate matter is evacuated, contrast infusions are delivered and blood pressures are monitored, and the lumen of the guide catheter 204 is not used for these functions.

As shown in FIG. 1D, in an embodiment of the multi-lumen elongate tube 102 two PTFE tubes comprising a main liner tube 107 and an flattened oval inflation tube 111 are provided. These tubes may be chemically etched to make them more bondable. These tubes may then be covered with an encapsulation material, for example, PEBAX, to create the composite, multi-lumen elongate tubular member 102 depicted in FIG. 1A. In this embodiment, the encapsulation layer may be a PEBAX tube 112 that is loaded over the assembly of the main tube 107 and the inflation tube 111. In an alternative embodiment, the encapsulation material covering the main tube may be different for the distal and proximal regions of the main tube, for example PEBAX 72D may be used to cover the proximal region of the tube while PEBAX 55D may be used to cover the distal region of the tube 107. In such an embodiment, the distal region of the tube may be 32 cm in length, alternatively, the distal region may be 20-45 cm in length. In addition main tube 107 may further comprise a kink resistant coil 108 surrounding the main tube 107. The PEBAX tube 112 may then be melted down to fill around the inflation tube 111, and impregnate the coil 108 and melt to the outside of the main tube 107. This process is sometimes called "reflowing". The melted PEBAX may then bond to the etched surfaces. Alternatively, the melting of the PEBAX encapsulation may be facilitated by the use of a separate heat shrink tubing (not shown) which is loaded over the initial PEBAX tube, and the whole thing is put into an oven. Here, the heat shrink will shrink at a temperature above the melt temp of the PEBAX and the melted Pebax will be forcibly squeezed around the entire outside of the inflation tube 111 and into the coil 108, resulting in a composite, mutli-lumen elongate tubular member.

It is contemplated that the multi-lumen tube 102 may be sized to fit within a 6 French guide catheter, alternatively a 7 French guide catheter, alternatively an 8 French guide catheter or other sized guide catheters. In an embodiment sized to fit with in a 6 French guide catheter, the main liner tube 107 may have, for example, an inner diameter of 0.052 inches and a wall thickness of 0.0015 inches, alternatively the inner diameter may range from 0.048 to 0.056 inches and/or the wall thickness may range from 0.001 to 0.004 inches. In such an embodiment, the inflation tube 111 may have an inner diameter of 0.006 inches, flattened to an oval shape with an inner diameter of 0.0025 inches and a wall thickness of 0.0015 inches, alternatively, the wall thickness may range from 0.001 to 0.004 inches and/or the inner diameter may range from 0.003 to 0.10 inches which may have no flattening or be flattened to an oval shape with as small as 0.002 inner diameter. In such an embodiment, the encapsulation layer 112 may have a thickness such that the outer diameter of the multi-lumen tube 107 is 0.064 inches, alternatively the outer diameter may range from 0.060-0.070 inches. In an embodiment sized to fit within a 7 French, 8 French or other sized guide catheter, it is further contemplated that ranges for the dimensions of the elements of the multi-lumen tube would be adjusted corresponding to the inner dimension of the guide catheter.

As depicted in FIGS. 3A and 3B, the kink resistant coil 108, comprising for example ribbon wire, may be wound directly onto the main tube 107 or expanded from a wound state and slidingly placed over the main tube 107. Here, the proximal and distal ends of coil 108 may then be wound so that the coil wraps are touching and welded together by one or more laser welds, for example as depicted herein three laser welds 308, to secure each end of the coil 108 and prevent it from unwinding. The kink resistant provides for the elongate tubular member to be highly flexible as well as kink resistant. The main tube 107, including the surrounding kink resistant coil 108, may then be bonded with an inflation tube as described above to create a multi-lumen elongate tubular member for use in the evacuation sheath assembly. In an alternative embodiment, the kink resistant structure may be a braid.

FIG. 1C illustrates in more detail the distal end of the evacuation sheath assembly 100. The soft distal tip 107 is secured to the distal end of the main tube 107 and the distal end of the expandable member 104 by suitable means such as thermal bonding. The soft tip 107 is preferably formed of a relatively soft PEBAX such as 35D and loaded with radiopaque material such as Barium Sulfate. Such a tip allows interventional devices such as stent delivery balloon catheters to be easily withdrawn back through the tip after their balloons have been inflated and subsequently deflated and "winged out". During retraction of the "winged out" balloon, the soft tip 107 can deform and dilate to help fold up the "winged out" balloon into the main lumen 106 of the evacuation sheath assembly 100.

The expandable member 104 is preferably blow-molded and attached to the multi-lumen elongate tubular member 102 with suitable means such as thermal bonding. Further details of preferred balloon materials and methods of fabrication may be found is U.S. patent application Ser. No. 10/214,712, filed on Aug. 9, 2002 and published as US2003/0050600, U.S. patent application Ser. No. 09/8940,896, filed on Aug. 29, 2001 and published as US2002/0165574 and U.S. patent application Ser. No. 09/845,162, filed on May 1, 2001 and published as US2002/0165598 all of which are incorporated in their entirety, herein.

As shown in FIG. 2, the multi-lumen elongate tubular member 102 is sized to fit inside a guide catheter 204 and to have a distal end 105 advanced beyond the distal opening of the guide catheter into a patient's blood vessel 200 while the proximal end 103 remains extending outside of the patient during use. The outer surface of the elongate tubular member 102 may be coated with a lubricious coating to facilitate movement through the lumen of the guide catheter 204. The lubricious coating may cover the distal 10 cm in length of the elongate tubular member, alternatively the coating may cover 20 cm, alternatively 30 cm, alternatively 40 cm and up to the entire length of the elongate tubular member. In an alternative embodiment, the outer surface of the expandable member 102 may also be coated with a lubricious coating to further facilitate delivery through the lumen of catheter 204. Note that FIG. 2 illustrates the embolic protection system at a particular point in time, namely after a stent has been positioned in the region of interest 206.

In use, the multi-lumen elongate tubular member 102 may be advanced through a guide catheter 204 over a guide wire 202 to extend distally from distal end of the guide catheter 204 into a patients blood vessel 200, in a fashion similar to that described in cross referenced U.S. patent application Ser. No. 10/214,712, Ser. No. 09/8940,896 and Ser. No. 09/845, 162 previously incorporated herein by reference. The guide wire 202 preferably only extends initially to the region of interest 206 (e.g. the blockage or lesion), but alternately the guide wire 202 may be advanced beyond the region of interest 206 initially. The multi-lumen elongate tubular member 102 is further advanced until the expandable member 104 is proximal to the region of interest 206. The expandable member may then be expanded to occlude blood flow in the region of interest 206. Once occluded, contrast may be infused via the main lumen 106 into the blood vessel. An inflation syringe 211 may be attached to the manifold 130 of the main lumen 106 via an aspiration tube 131 and stopcock 132 to provide a contrast agent or other fluids, such as saline or therapeutic agents, to the region of interest via the main lumen 106. An interventional catheter such as a stent delivery catheter may be introduced over the guide wire 202, through the main lumen 106 to deliver a stent to the region of interest 206. The interventional catheter may then be removed from the main lumen 106. A vacuum may be induced within the main lumen 106 of the multi-lumen elongate tubular member 102 using a evacuation syringe 210 connected to the main lumen 106 via the stopcock 132 and aspiration tube 131 on the manifold 130. The vacuum will draw the embolic particulate matter 207 from the blood vessel 200 and through the main lumen 106 into the evacuation syringe 210. After the embolic particulate matter is removed, the expandable member 104 may be deflated and the multi-lumen elongate tubular member 102 may be withdrawn from the blood vessel 200. Alternatively, a contrast dye may be introduced into the region of interest via the previously described method to insure that all of the embolic particulate matter was removed and that the region of interest is sufficiently treated before deflating the expandable member and removing the multi-lumen elongate tubular member 102.

An unrecognized advantage of this design, wherein the main lumen 106, which is used for evacuation, extends the full length of the elongate tubular member 102, vs. "short lumen" designs wherein the evacuation lumen was partially defined by the guiding catheter, as described in U.S. patent application Ser. No. 10/214,712, Ser. No. 09/8940,896 and Ser. No. 09/845,162 previously incorporated herein by reference, is that the evacuation lumen is less obstructed. In this embodiment, the full length main lumen typically houses only a guide wire 202 inside, and therefore particulate doesn't catch and hang up on any of the protruding surfaces while being evacuated through the main lumen. In the short lumen designs, the particulate could hang up, particularly at "crossovers" of the guide wire and the proximal shaft and be at risk of redelivery into the circulation during subsequent contrast injections. So even though this design uses the main lumen 106 of the elongate tubular member 102 for the evacuation lumen, which has a smaller full-length cross section for a given guiding catheter compatibility (since none of the main lumen is defined by the guide catheter lumen), it is more effective at particulate removal in the clinical setting.

It is still desirable, however, to maximize the inner diameter of the evacuation lumen 106 to the extent possible, primarily for compatibility with larger stent delivery systems being advanced through the evacuation lumen. For a particular guide catheter compatibility, for example 6 French, 7 French or 8 French, that means making the outer diameter of the elongate tubular member 102 close to the guide catheter inner diameter, adding lubricious coating to the outer surface of the elongate tubular member 102, and making the walls of the elongate tubular member 102 as thin as possible. To help facilitate making the wall thin, a gas instead of liquid is used to inflate the expandable member. Gas has a much lower viscosity than a liquid and therefore enables use of a smaller inflation lumen 110 in the elongate tubular member 102. As shown in FIGS. 1B and 2, a special gas inflation system 120 may be connected to the inflation lumen 110 via a tubular member 122 to quickly and safely accomplish delivery of a gas to the expandable member. Here, the tubular member 122 of the gas inflator 120 has an inner diameter corresponding to the diameter of the inflation lumen 110 for fluid communication therebetween.

Figure 5:
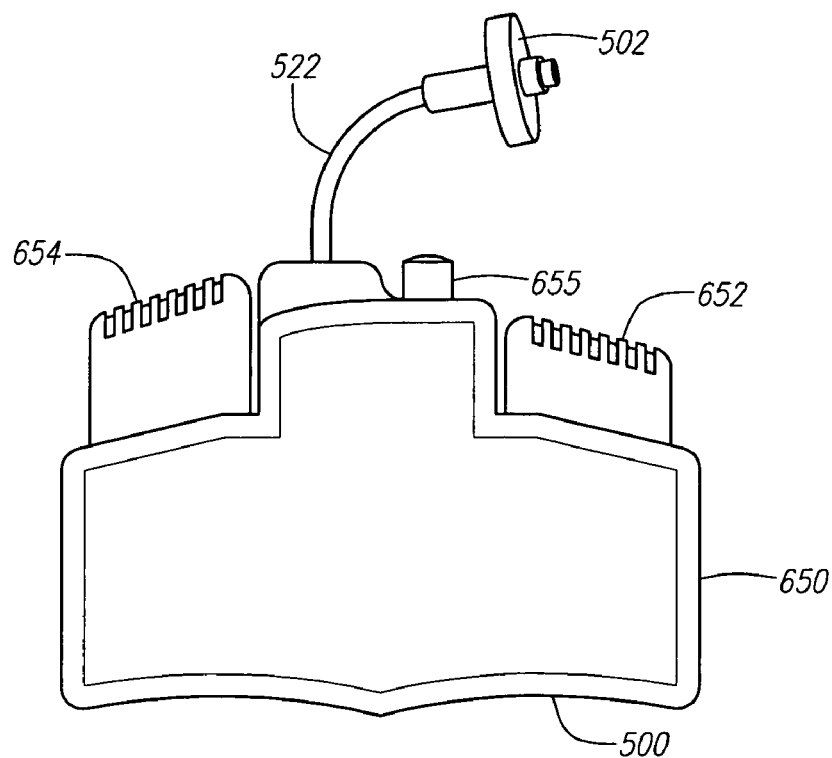
FIG. 5 illustrates an overview of an embodiment of a gas inflator according to the present invention.

In one embodiment, shown in FIG. 6, the gas inflation system 120 comprises a high pressure gas cartridge 600, a shuttle mechanism 610, a first pressure relief mechanism 620 and a second pressure relief mechanism 630. As depicted in FIG. 5, the gas inflation system may be enclosed within a housing 650 and may further include an inflation button 652 and a vacuum button 654 and a pressure indicator window 655. The inflation button 652 and vacuum button 654 are operably connected to the shuttle mechanism 610 for controlling movement of the shuttle mechanism 610 and thereby controlling the flow of gas within the gas inflation system, inflation lumen and expandable member. In addition, as depicted in FIG. 5, an alternative embodiment of the gas inflation system may further include an in-line filter 502 connected in-line with a tube 122 leading from the gas inflation system 600 to the inflation lumen of the expandable member. This serves to guard against passage of contaminants such as spores, which may be present in the gas cylinder, to the expandable member. This filter is preferably a 0.20 micron mesh.

Figure 6A:
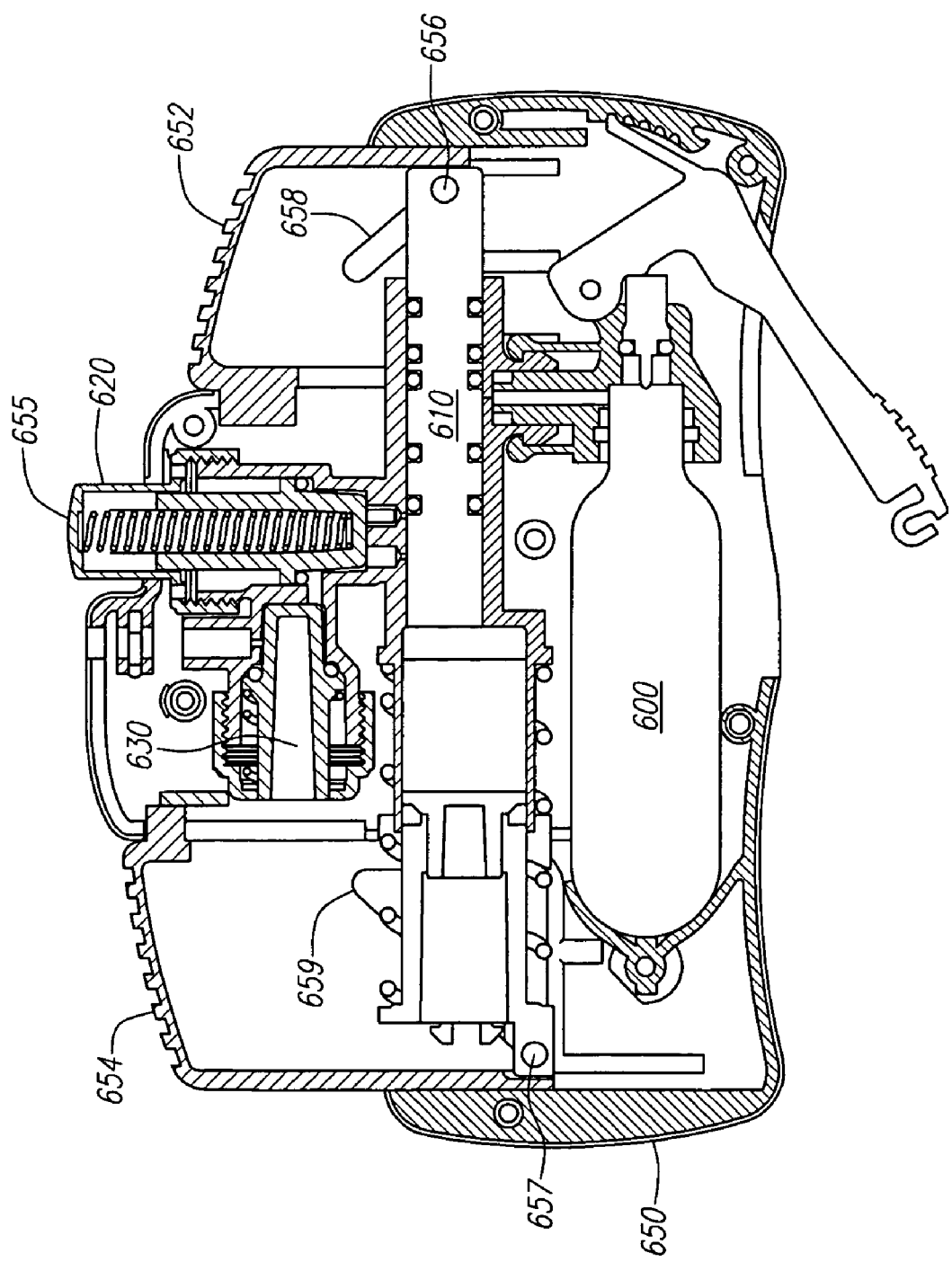
FIG. 6A illustrates a cross-sectional view of an embodiment of a gas inflator according to the present invention.
Figure 6B:
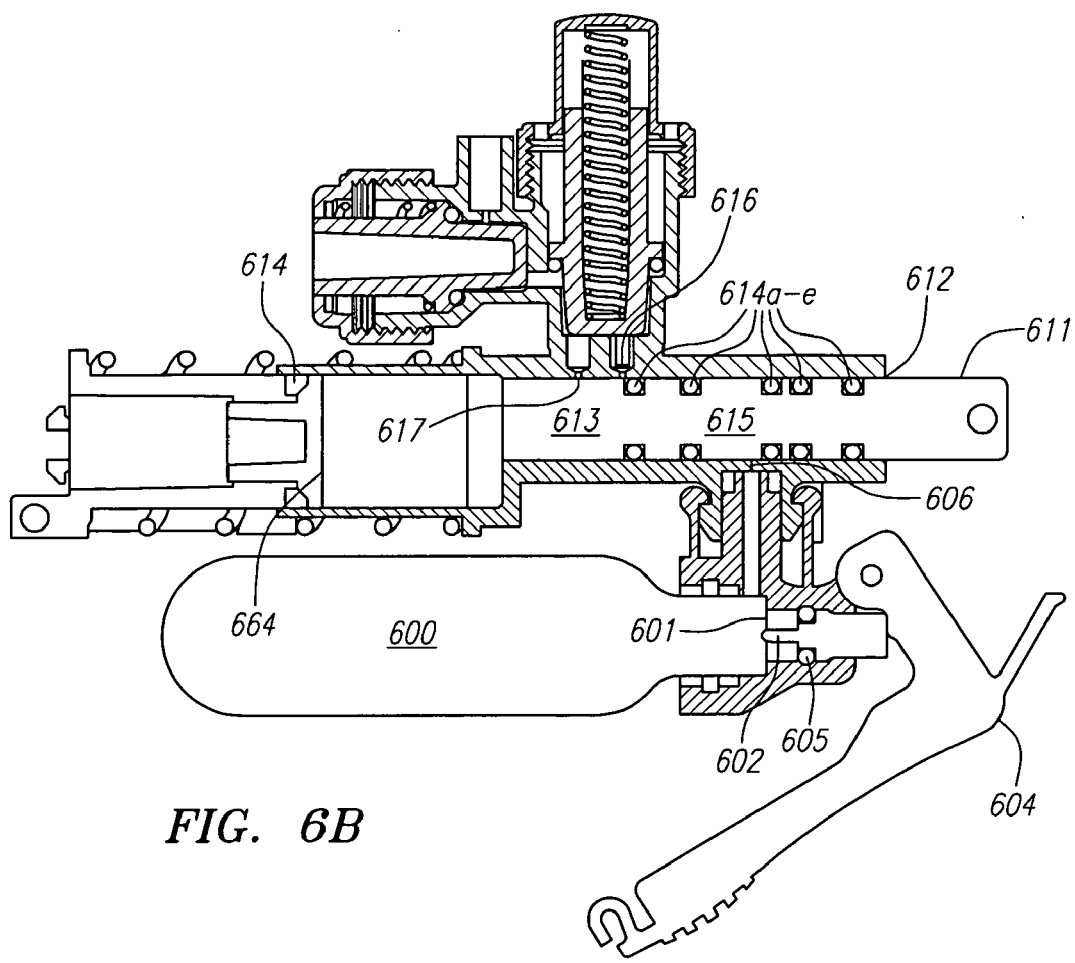
FIG. 6B illustrates a cross-sectional view of an embodiment of the high pressure gas source and gas delivery mechanism of a gas inflator according to the present invention.

FIG. 6B shows the high pressure gas cartridge puncture mechanism and the shuttle mechanism in more detail. The puncture mechanism includes a lever 604 and a puncturing spear 602, which are shown in the pre-puncture condition. The high pressure gas cartridge is connected to the puncturing spear 602 and an inlet port 606 in fluid communication with the shuttle mechanism 610. Actuation of the lever 604 pushes the puncturing spear 602 into the seal 601 of the gas cartridge 600. The spear includes a sharpened conical tip, and a stem. The maximum diameter of the conical tip is larger than the diameter of the stem. This allows free passage of the gas past the sharpened tip once the tip has punctured and passed through the seal of the cartridge, allowing the high pressure gas to flow into the shuttle mechanism 610 via an inlet port 606 in fluid communication with the shuttle mechanism 610. The high pressure gas cartridge may contain $CO_2$ gas, alternatively, other gases such as nitrous oxide could be used. The contents of the gas cartridge are typically maintained at a high pressure, for example a $CO_2$ cartridge may be maintained at 900 psi. At this pressure, much of the contents of the cartridge are actually liquid $CO_2$. An advantage of liquid $CO_2$ is that the $CO_2$ is further compressed so that a larger volume of $CO_2$ may be stored in a smaller space. Thus, the O-ring 605 is desirable in the puncture mechanism to prevent the high pressure gas contents from leaking.

The shuttle mechanism 610 of the present embodiment, as depicted in FIG. 6B, comprises a cylindrical shuttle chamber 612, within which are the shuttle and a series of seals 614. The shuttle chamber 612 is essentially the annular space between the shuttle 611 and the walls defining the shuttle chamber. The chamber of the shuttle mechanism 612 further includes a series of seals 614 spaced apart to divide the chamber into at least two primary chambers, a pressure chamber 615 and a vacuum chamber 616. The pressure chamber 615 and vacuum chamber 616 are not in fluid communication and are isolated from one another and from the outside by the seals 614a-f. According to one aspect of the invention, the pressure chamber may be defined by two spaced apart seals, for example o-ring seals. Alternatively, as depicted in FIG. 6B, the pressure chamber may further comprise one or more additional adjacent seals providing a safe guard against leakage of the high pressure gas. The seals 614a-f may be o-ring seals. Alternatively, the seals may be any suitable seal for isolating fluid communication between two defined chambers. The seal 614f, defining the boundary of the vacuum chamber 613, may alternatively be a one way bypass seal in order to provide a means for removing the air from the chamber to create a vacuum. In addition, three ports preferably access the shuttle chamber, a cartridge inlet port 606 which allows the high pressure gas from the cylinder to enter the shuttle chamber, a high resistance outlet 616 which conveys the gas from the pressure chamber to the pressure relief mechanisms 620 and 630, the inflation lumen and the expandable member, and a vacuum port 617 through which gas is drawn out of the inflation lumen and expandable member into the vacuum chamber 613 when a vacuum is created therein.

Figure 7:
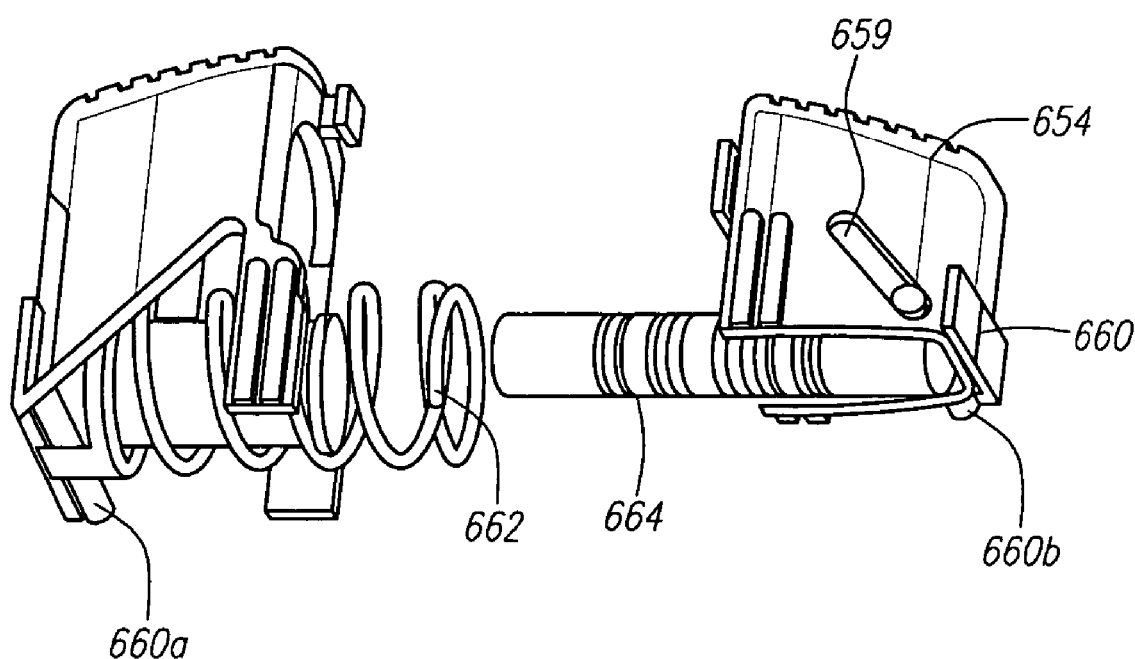
FIG. 7 illustrates an embodiment of a control switch for controlling movement of the shuttle mechanism and regulating gas flow within a gas inflator according to the present invention.

In use, the shuttle mechanism 610 is transported longitudinally to alternately place the pressure chamber 615 in fluid communication with the cartridge inlet port and then the high resistance outlet 616, as well as the vacuum chamber 613 in fluid communication with the vacuum port 613. As shown in FIG. 6A, an embodiment of a shuttle transport mechanism may include an inflation button 652 and deflation button 654 operably connected to the shuttle mechanism 610 via cooperating connective elements located on the shuttle mechanism and the inflation and deflation buttons which are slidably coupled. For example, pins (shown on FIG. 7) extending horizontally from holes 656 and 657 on the ends of the shuttle mechanism 610 may be slidably housed within corresponding biased grooves 658 and 659 in the inflation 652 and vacuum 654 buttons. As depicted in FIG. 7, when button 654 is actuated, it moves vertically. As the button 654 moves, the biased groove 658 formed in the side walls of the button will also move vertically, resulting in the translation of horizontal location of the groove in any given plane. Thus, the attached pins 660*a* and 660*b* of the shuttle mechanism will be shifted longitudinally, corresponding to vertical movement of the button 654, as it rides in the biased groove 659. As the shuttle mechanism is translated longitudinally, the pressure chamber 615 and vacuum chamber 613 are alternately placed in fluid communication with the outlet port 616 and vacuum port 617 in order to deliver a bolus of gas from the pressure chamber 615 via the outlet port 616 or alternately, to draw any residual gas from the inflation lumen and expandable member into the vacuum chamber 613 via the vacuum port 617. In addition, the vacuum button 654 depicted in FIG. 7 further includes an internal spring 662 and a vacuum piston 664 for creating a vacuum in the vacuum chamber of the shuttle mechanism. In use, as depicted in FIGS. 6B and 7, when the vacuum button 654 is depressed, the vacuum piston 664 is also displaced to force gas out of the vacuum chamber 613 via a one way bypass seal 614*f*. The spring 662 which was compressed during actuation of the vacuum button 654 then expands, returning the vacuum piston 664 to its initial location and creating a vacuum within the vacuum chamber 613.

Figure 6C:
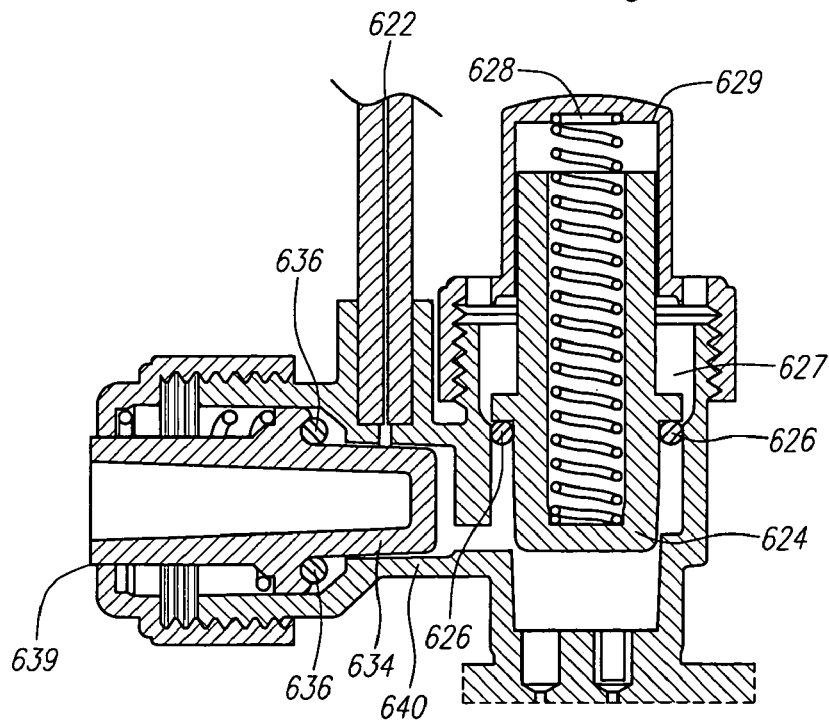
FIG. 6C illustrates a cross-sectional view of an embodiment of a pressure relief valve/pressure indicator and an inflation communication outlet of a gas inflator according to the present invention.

The outlet port 616 and vacuum port 617 are additionally in fluid communication with at least one pressure relief valve 620. Alternatively, a second pressure relief valve 630 may be provided. Two relief valves provides a safety redundancy in the case of a failure of a single relief valve, however, it is contemplated that a single relief valve could also be utilized. Both relief valves could be similar to the primary relief valve 630 described below, or alternatively, as depicted in FIG. 6C and described herein, a pressure indicator may be incorporated into one of the relief valves, hereinafter referred to as an indicator relief valve 620. The indicator relief valve 620 and a primary pressure relief valve 630 are both in communication with the shuttle chamber (not shown) via outlet ports 616 and 617, as described above. The indicator valve 620 and pressure relief valve 630 serve to regulate the gas pressure within them by releasing excess gas volume above a desired pressure, thereby enabling an inflation communication outlet 622 that is in fluid communication with valves 620 and 630 to deliver gas to the expandable member at a controlled pressure. The pressure relief mechanism thus assists the gas inflator system to efficiently store the gas in a high pressure form then transform the high pressure gas source into a controlled low pressure gas for safe delivery to the expandable member.

As embodied herein, the indicator relief valve 620 includes an indicator poppet 624, a sealing o-ring 626, a spring 628, and a cap 629. When pressurized gas enters into the pressure relief mechanism, it drives the indicator poppet 624 up, which compresses the spring 628. Once the sealing o-ring rises above the bypass 627 excess gas will leak out, maintaining the gas within the pressure relief mechanism at the desired pressure. In an embodiment as depicted herein, the bypass may be created, for example, by an expansion of the housing to create a gap between the o-ring seal and the housing once the o-ring rises above the expanded section of the housing. The movement of the indicator poppet 624 is also a visual indicator that the pressure relief mechanism (and subsequently the inflation lumen and inflatable member of the catheter) is pressurized, as opposed to being at ambient pressure, or negative vacuum pressure. The pressure at which the indicator relief valve 620 will leak excess gas is determined by the spring stiffness properties, as well as the dimensions of the poppet 624 and sealing o-ring 626. In addition, relatively small adjustments may be made by adjusting the relative tightness of the cap 629, which is screwed onto the housing.

The primary relief valve 630 includes a primary poppet 634, o-ring 636, spring 638, and a cap 639. Unlike the indicator poppet 624, which requires the o-ring to actually rise above the bypass before gas will leak, the primary poppet 634 preferably leaks excess pressurized gas as soon as the poppet 634 begins to move relative to the housing 640. The spring 638 is in a pre-compressed condition against the primary poppet 634 and o-ring 636. When the pressure force on the poppet exceeds the force of the compressed spring 638, the poppet 634 will move slightly, resulting in leakage until the pressure within the primary relief valve drops below the desired pressure.

In use, the desired leak pressure of each relief valve can be the same, or alternatively, the indicator relief valve 620 may be set slightly lower than the primary relief valve 630. In this manner, most or all of the excess pressurized gas will leak from the primary relief valve 630. For example, in an embodiment of the inflation system for use with the embolic protection catheter embodiments described here, the primary relief valve may be set to leak at about ⅔ atmosphere, and the indicator relief valve may be set slightly higher, for example, approximately 0.5 to 1 psi higher.

FIGS. 8A-H illustrate a schematic representation of the shuttle mechanism and operation of the gas inflation system. Like numbers depict the components as described in the gas inflation system described above. As depicted herein, the shuttle mechanism 610 controls the inflation of the expandable member (not shown) with a gas, for example $CO_2$ or nitrous oxide or another suitable gas, and subsequent deflation of the expandable member when desired.

As previously described, the shuttle mechanism 610 comprises a cylindrical shuttle chamber 612, within which are the shuttle 611 and a series of o-ring seals 614*a-e*. The shuttle chamber 612 is essentially the annular space between the shuttle and the walls defining the shuttle chamber. For ease in illustration, this "gap" is shown rather large in these figures. The o-rings 614*a-e* are used to divide the shuttle chamber into two primary chambers, the pressure chamber 615 and the vacuum chamber 613. In addition, the vacuum chamber is further defined by a one-way bypass seal attached to a vacuum piston 664. Three ports access the shuttle chamber, a cartridge inlet port 606 which allows the high pressure gas from the cylinder (not shown) to enter, a high resistance outlet port 616 which conveys the gas from the pressure chamber 613 to the pressure relief mechanism 620 and the expandable member (not shown), and a vacuum port 617 through which gas is drawn out of the expandable member into the vacuum chamber 613 when a vacuum is created.

Figure 8A:
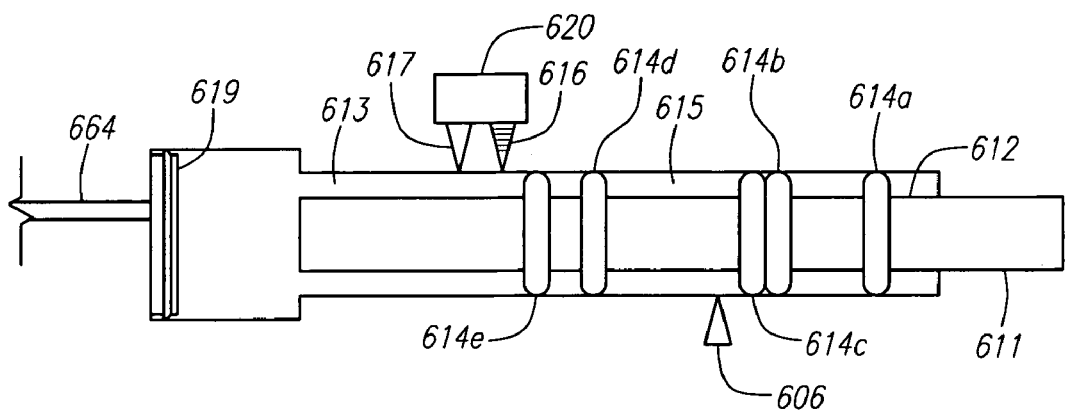
FIG. 8A-H illustrate a schematic diagram of an embodiment of a shuttle mechanism in use according to the present invention.
Figure 8B:
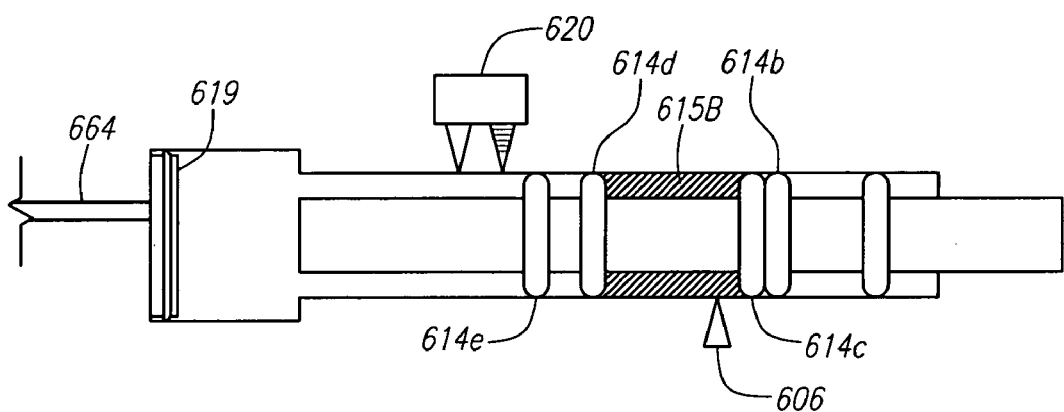

In FIG. 8A, the shuttle mechanism is in the initial condition, wherein the pressure chamber 613, vacuum chamber 615 and expandable member are all at ambient pressure. In FIG. 8B, the pressure cartridge (not shown) has been punctured, which allows the high pressure gas to enter and fill the pressure chamber 615 via the cartridge inlet port 806. The pressure chamber 615B is shaded to depict the bolus of high pressure gas filling the pressure chamber. O-rings 614*c* and 614*d* keep the high pressure gas confined to the pressure chamber 615. In an alternative embodiment, as depicted herein, an additional o-ring 614*b* may be placed adjacent to 614*c* to provide an additional safeguard against the high pressure gas leaking from the pressure chamber. This additional safeguard may be desired since $CO_2$ cartridges, for example, are typically pressurized to 900 psi, and include a portion of liquid $CO_2$ which keeps the pressure relatively constant as the gas volume is consumed. Once the pressure chamber is placed within fluid communication with the gas cartridge via inlet port 606, the pressure chamber becomes pressurized to the same pressure as the cylinder, typically about 900 psi. The shuttle mechanism may now be ready to deliver the bolus of gas contained within the pressure chamber 615 to the inflation lumen and expandable member via the high resistance outlet port 616.

Figure 8C:
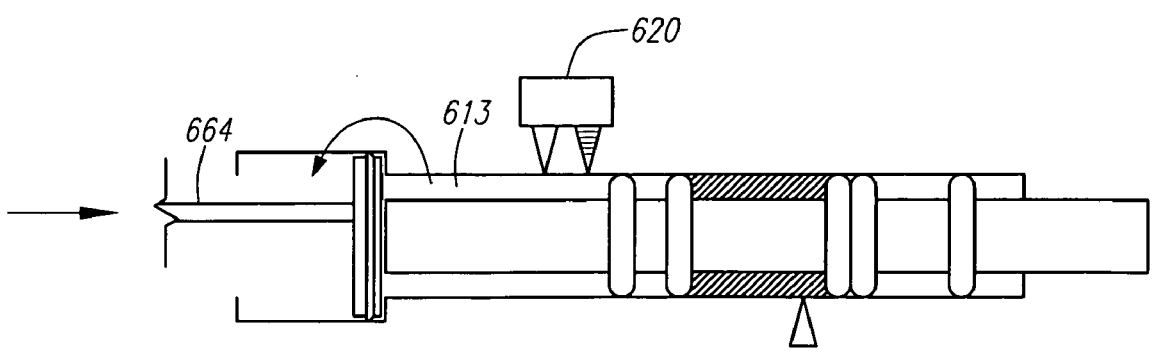
Figure 8D:
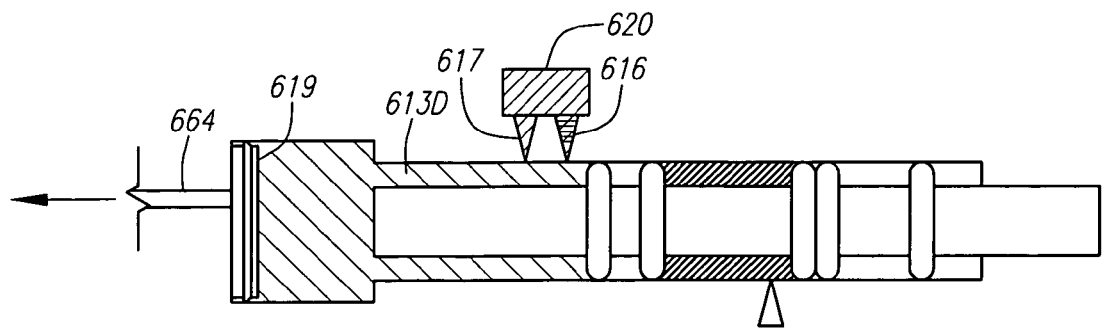

In an alternative embodiment, it may be desirable to "prep" the inflation lumen and expandable member to remove most of the ambient air in the expandable member and all gas passageways, including the inflation lumen, in communication therewith. This additional step of "prepping" the inflation lumen and expandable member is depicted in FIGS. 8C and 8D. In FIG. 8C, the vacuum piston 664 is advanced into the vacuum chamber 613. The one-way bypass o-ring 619 allows the ambient pressure air to bypass or vent out, indicated by the arrow. A return spring (not shown) draws back the vacuum piston 664, creating a vacuum in the vacuum chamber, shown in Figure D by the cross-hatch vacuum pattern in the pressure chamber 613D. The vacuum chamber 613D is in fluid communication with the inflation lumen and the expandable member via the high resistance outlet 616 and the vacuum port 617, thus this vacuum may draw out a significant portion of the air from the catheter balloon and inflation lumen. A majority of the air is drawn out through the pressure relief mechanism (not shown) and the vacuum port 617; however, a small amount of air is also drawn through the high resistance outlet 616, as this is in fluid communication with the vacuum chamber at this time. After this step, the vacuum chamber 613, expandable member and all passageways therebetween will be evacuated. In this embodiment, the dimensions of the vacuum chamber were chosen such that a single actuation of the vacuum piston would result in an acceptable strength vacuum. In an alternative embodiment, the vacuum piston may be actuated multiple times to enhance the strength of the vacuum.

Figure 8E:
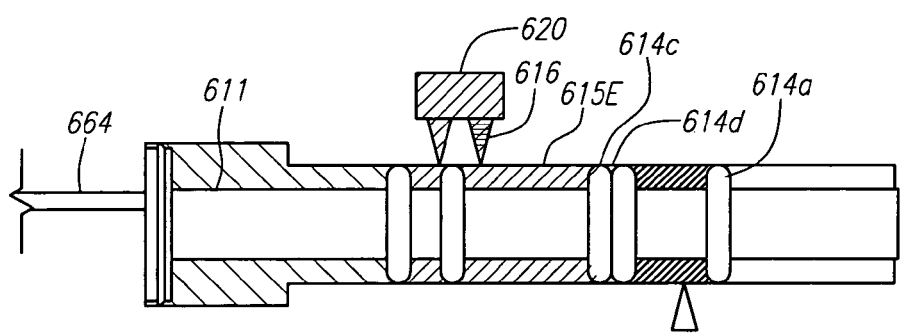

To inflate the expandable member with gas, the shuttle mechanism may be moved as shown in FIG. 8E. This translation carries ("shuttles") the pressure chamber 615E into communication with the high resistance outlet 616. The high pressure gas may then pass through the high resistance outlet 616 into the pressure relief mechanism 620 and into the expandable member. As previously mentioned, the pressure relief mechanism guards against over pressurization of the expandable member by venting excess gas before it could over-inflate the expandable member. In addition, the dimensions of the shuttle mechanism 610 may be designed such that such that the volume of the pressure chamber 615E is significantly smaller than the combined volume of the pressure relief mechanism, expandable member, and all passageways therebetween. This will minimize the volume of excess gas that must be vented from the pressure relief mechanism, a further safety feature for a gas inflator system. In an alternative embodiment, the shuttle mechanism may be designed such that when the pressure chamber delivers a volume of gas to the pressure relief mechanism, little to no excess gas needs to be released to result in the expandable member being pressurized to its target desired pressure, in this case, preferably about ⅔ atmosphere gauge pressure.

The high resistance outlet 616 controls the flow rate of the high pressure gas from the pressure chamber 615E such that the pressure relief mechanism is not overwhelmed with an excessively high pressure spike. After the expandable member is inflated to the desired target pressure, the pressure chamber, pressure relief mechanism, expandable member and inflation lumen are all at that same relatively low pressure of approximately ⅔ atmosphere, and filled with gas, as noted by the low pressure pattern in the FIG. 8E. During this step, the dead-spaces between some of o-rings 614*b* and 614*a* may have also become pressurized, as indicated by the high pressure pattern shown in FIG. 8E as a result of coming into fluid communication with the cartridge inlet port 606. The rightmost o-ring 614*a* now prevents leakage of the high pressure cartridge contents out the right side of the pressure chamber, and the double o-rings 614*b* and 614*c* serve as a redundant barrier between the high pressure cylinder and the expandable member at this time. If there were only one o-ring there and it somehow failed, high pressure $CO_2$ could potentially over-pressurize the expandable member and cause rupture and excessive gas leakage.

Figure 8F:
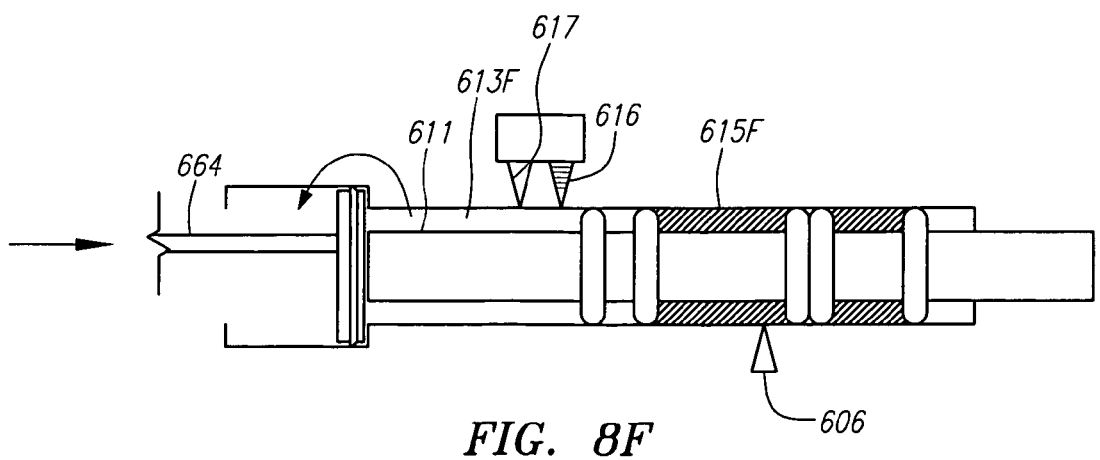
Figure 8G:
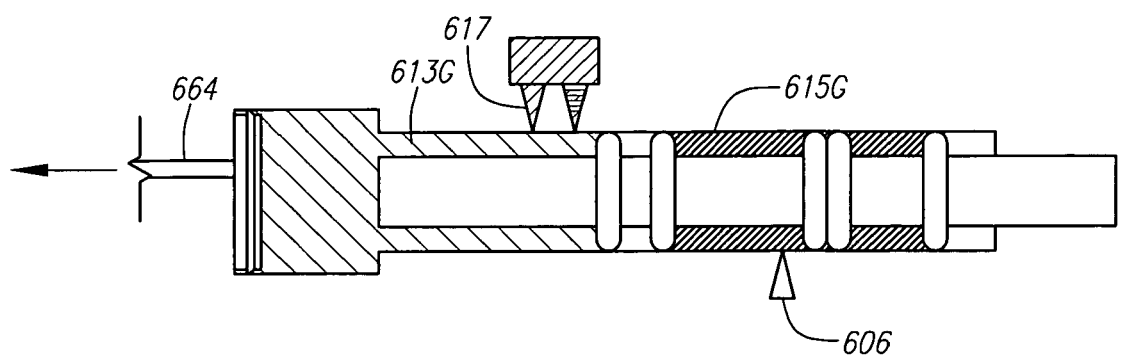

To deflate the balloon and evacuate the $CO_2$ gas, the evacuation piston is advanced, as shown in FIG. 8F. In this step, the piston 664 initially abuts the shuttle, resulting from the prior translation of the shuttle to deliver the gas, as shown in FIG. 8E. When the vacuum button (not shown) is depressed, the translation of the piston 664 also translates the shuttle 611. The pressurized expandable member (and inflation lumen, pressure relief mechanism) will vent the gas once the vacuum port 617 is exposed to the vacuum chamber 613. The gas may vent past the one-way bypass o-ring 619 attached to the vacuum piston 664, resulting in the vacuum chamber 613F, pressure relief mechanism and the expandable member returning to ambient pressure. When the vacuum piston 664 is released, a vacuum is again formed in the vacuum chamber 613G, and the remaining ambient air in the expandable member and inflation lumen may be drawn out via the vacuum port 617, as depicted in FIG. 8G. The action of translating the shuttle 611 also brings the pressure chamber 615F/615G back to the position where it is in fluid communication with the gas cartridge input port 606 and thereby gets refilled with a bolus of high pressure gas by the high-pressure gas cylinder.

Figure 8H:
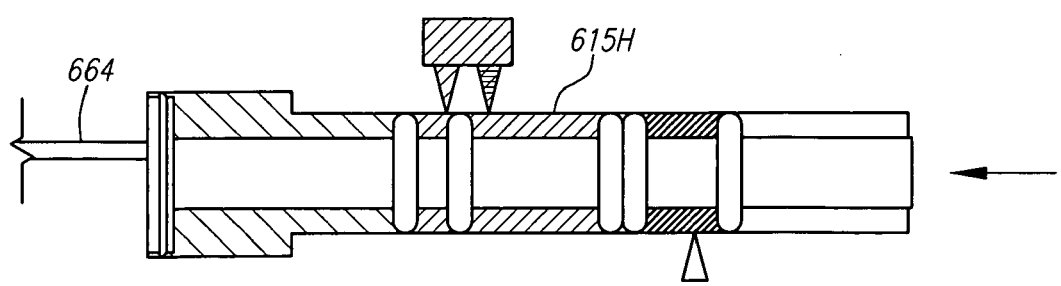

To re-inflate the expandable member, the shuttle 611 is translated again to the left, as shown in FIG. 8H. As in FIG. 8E, the high pressure bolus in the pressure chamber 615H is brought into communication with the pressure relief mechanism and the inflation lumen leading to the expandable member via the high resistance outlet 616. The expansion of the bolus of gas into a larger volume and the venting of gas by the one or more pressure relief valves results in a relatively low pressure inflation of the expandable member, for example in this embodiment of about ⅔ atmosphere. In addition, repeated deflations and inflations may be performed by repeating the steps depicted in FIGS. 8F, 8G, and 8H.

Relative to inflation of the expandable member in the vasculature of the patient, it is preferable to carry out the "prepping" steps depicted in FIGS. 8A-8D prior to introduction of the catheter into the patient. This places the balloon in a vacuum condition, which helps minimize profile of the deflated balloon. However, in an alternative method of use, it is also possible to carry out the initial inflation and deflation of the expandable member, steps corresponding to FIGS. 8E, 8F, and 8G, as well, prior to introduction of the catheter into the patient. The reason is that the inflation depicted in FIG. 8E is the first inflation of the balloon. Here, there will be a small residual amount of air in the balloon at this step, and if the balloon contents leak out, some air also leaks out, which is undesirable. The amount of residual air at this step is dependent on the relative volumes of the vacuum chamber and the catheter balloon and the passageways leading thereto, and may be clinically insignificant. However, after an additional vacuum and pressurization step, the residual air in the expandable member as of the inflation step of Fig. H will be significantly less, as the expandable member has already been "primed" with CO2 gas from the first inflation shown in Figure E.

Having thus described a preferred embodiment of a device and methods for embolic protection during vascular intervention, it should be apparent to those skilled in the art that certain advantages of the within system have been achieved. It should also be appreciated that various modifications, adaptations and alternative embodiments thereof may be made within the scope and spirit of the present invention. It is intended that the specification and examples be considered as exemplary only, with a true scope and spirit of the invention being defined by the following claims.

We claim:

1. An evacuation sheath assembly comprising:
a first elongate tubular member having a distal end, a proximal end and an evacuation lumen extending therebetween, wherein the evacuation lumen is configured to be placed in fluid communication with a bloodstream;
a second elongate tubular member having a distal end, a proximal end and an inflation lumen extending therebetween;
an expandable sealing member mounted on the distal end of the first elongate tubular member and having a chamber in fluid communication with the inflation lumen;
a gas inflator having a pressure regulating mechanism comprising a vacuum chamber, a pressure chamber, and a shuttle configured to move between a first position in which the pressure chamber is in fluid communication with a high pressure gas source, a second position in which the pressure chamber is in fluid communication with the inflation lumen, and a third position in which the vacuum chamber is in fluid communication with the inflation lumen.

2. The device of claim 1, wherein the expandable sealing member is a balloon.

3. The device of claim 1, further comprising a soft tip mounted on the distal end of the first elongate tubular member.

4. The device of claim 3, wherein the soft tip is secured to the distal end of first elongate tubular member and the distal end of the expandable member.

5. The device of claim 1, further comprising a kink resistant coil surrounding the first elongate tubular member.

6. The device of claim 5, wherein one or more adjacent turns of the kink resistant coil are laser-welded together.

7. The device of claim 5, wherein the second elongate tubular member is mounted adjacent to the first elongate tubular member on the kink resistant coil.

8. The device of claim 7, further comprising an encapsulation layer surrounding the kink resistant coil and the second elongate tubular member.

9. The device of claim 8, wherein the encapsulation layer is made of a polyether block amide.

10. The device of claim 1, wherein the evacuation sheath is sized to have an outer diameter substantially the same size as the inner diameter of a guide catheter and wherein the outer diameter of the evacuation sheath is covered with a lubricious coating.

11. The device of claim 10, wherein the expandable member is covered with a lubricious coating.

12. The device of claim 10, wherein the evacuation sheath is sized to have an outer diameter substantially the same size as a 6 French guide catheter.

13. The device of claim 10, wherein the evacuation sheath is sized to have an outer diameter substantially the same size as a 7 French guide catheter.

14. The device of claim 10, wherein the evacuation sheath is sized to have an outer diameter substantially the same size as an 8 French guide catheter.

15. The device of claim 1, further comprising a third elongate tubular member slidably insertable through the evacuation lumen and extendable from an aperture of the evacuation lumen for positioning beyond the distal end of the evacuation lumen, wherein the third elongate tubular member has a proximal end, a distal end, a lumen extending therebetween, and an aperture disposed at the distal end for communicating said lumen with the bloodstream and is connected at the proximal end of the tube with an infusion means for delivering a fluid into the blood stream.

16. An evacuation sheath assembly, comprising:
a multi-lumen tubular member having an evacuation lumen and an inflation lumen;
an expandable member mounted on the multi-lumen member and having a chamber in fluid communication with the inflation lumen;
a gas inflator comprising a vacuum chamber, a pressure chamber, and a shuttle, the shuttle operable between a first position providing fluid communication between the pressure chamber and the inflation lumen, a second position providing fluid communication between the pressure chamber and a source of high pressure gas, and a third position providing fluid communication between the vacuum chamber and the inflation lumen.

17. The evacuation sheath assembly of claim 16, wherein the multi-lumen tubular member further comprises an infusion lumen connected with an infusion source and configured for delivery of a fluid.

18. The evacuation sheath assembly of claim 17, wherein the infusion lumen is positioned within the evacuation lumen.

19. The evacuation sheath assembly of claim 17, wherein the infusion lumen extends distal of a distal end of the evacuation lumen.

* * * * *